United States Patent
Shakespeare

(10) Patent No.: US 7,164,145 B2
(45) Date of Patent: Jan. 16, 2007

(54) MEASURING FIBER ORIENTATION BY DETECTING DISPERSION OF POLARIZED LIGHT

(75) Inventor: John F. Shakespeare, Kuopio (FI)

(73) Assignee: Honeywell International Inc., Morristown, NJ (US)

(*) Notice: Subject to any disclaimer, the term of this patent is extended or adjusted under 35 U.S.C. 154(b) by 0 days.

(21) Appl. No.: 11/127,742

(22) Filed: May 12, 2005

(65) Prior Publication Data

US 2006/0255300 A1    Nov. 16, 2006

(51) Int. Cl.
G01N 21/89    (2006.01)
G01N 21/21    (2006.01)
G01N 21/86    (2006.01)

(52) U.S. Cl. .................. 250/559.09; 250/559.05; 250/559.07; 250/225; 356/429; 356/238.1; 356/364; 162/198; 162/263

(58) Field of Classification Search .......... 250/225, 250/559.09, 559.45–559.49, 559.04–559.08; 356/429–431, 364–368, 370, 238.1; 162/198, 162/263, DIG. 11; 700/122, 127
See application file for complete search history.

(56) References Cited

U.S. PATENT DOCUMENTS

| | | | | |
|---|---|---|---|---|
| 3,807,868 A * | 4/1974 | Simila | ............... | 356/369 |
| 4,519,041 A | 5/1985 | Fant et al. | ............... | 364/552 |
| 4,654,529 A * | 3/1987 | Boulay et al. | ............... | 250/341.3 |
| 4,818,930 A | 4/1989 | Flemming et al. | ............... | 324/58.5 |
| 4,931,657 A | 6/1990 | Houston et al. | ............... | 250/559 |
| 4,955,720 A | 9/1990 | Blecha et al. | ............... | 356/429 |
| 5,104,488 A | 4/1992 | Chase | ............... | 162/198 |
| 5,138,878 A | 8/1992 | Cresson et al. | ............... | 73/159 |
| 5,324,475 A | 6/1994 | Okahashi | ............... | 264/555 |
| 5,475,233 A | 12/1995 | Fukuoka et al. | ............... | 250/559.1 |
| 5,581,637 A | 12/1996 | Cass et al. | ............... | 382/284 |
| 5,640,244 A | 6/1997 | Hellstrom et al. | ............... | 356/429 |
| 5,699,163 A | 12/1997 | Todoroki et al. | ............... | 356/445 |
| 5,764,874 A | 6/1998 | White | ............... | 396/155 |
| 5,852,449 A * | 12/1998 | Esslinger et al. | ............... | 345/473 |
| 5,982,498 A * | 11/1999 | Byatt et al. | ............... | 356/429 |
| 5,991,046 A | 11/1999 | Shakespeare et al. | ............... | 356/429 |
| 6,111,651 A | 8/2000 | Shakespeare | ............... | 356/429 |
| 6,295,393 B1 | 9/2001 | Naganuma | ............... | 385/11 |
| 6,441,904 B1 | 8/2002 | Shakespeare | ............... | 356/429 |
| 6,524,441 B1 * | 2/2003 | Ruf et al. | ............... | 162/198 |
| 6,606,394 B1 | 8/2003 | Park et al. | ............... | 382/108 |

(Continued)

FOREIGN PATENT DOCUMENTS

CA        2012351        9/1990

(Continued)

*Primary Examiner*—Stephone B. Allen
*Assistant Examiner*—Davienne Monbleau
(74) *Attorney, Agent, or Firm*—Narendra Reddy Thappeta

(57) ABSTRACT

An image-based technique that measures the orientation of fibers in a moving web of nonwoven material. At least four light spots on one side of the web are illuminated essentially simultaneously with at least four plane-polarized incident substantially perpendicular light beams having different polarization characteristics. Dispersion of the excident light spots is measured on the opposite side of the web along at least one linear section which is at a known angle relative to the plane of polarization of the corresponding plane-polarized incident light beam, wherein at least one such linear section lies substantially across the center of the transmitted excident light spot and extends substantially across the width of the transmitted excident light spot. Variations in the dispersion of the transmitted excident light spot for the at least four plane-polarized light beams are calculated, and the fiber orientation is estimated from the variations.

41 Claims, 15 Drawing Sheets

U.S. PATENT DOCUMENTS

| | | |
|---|---|---|
| 6,643,022 B1 | 11/2003 | Komppa ................ 356/445 |
| 6,717,675 B1 * | 4/2004 | Munch ................. 356/429 |
| 6,717,729 B1 | 4/2004 | Goto et al. ............ 359/485 |
| 6,743,337 B1 * | 6/2004 | Ischdonat ............. 162/198 |
| 6,799,083 B1 | 9/2004 | Chen et al. ............ 700/128 |
| 6,859,279 B1 | 2/2005 | Tabet ................... 356/369 |
| 2002/0039181 A1 | 4/2002 | Shakespeare et al. |
| 2002/0097320 A1 | 7/2002 | Zalis |
| 2002/0159618 A1 | 10/2002 | Freeman et al. |
| 2003/0144747 A1 | 7/2003 | Shakespeare |
| 2003/0156293 A1 | 8/2003 | Kazuhiko et al. |
| 2004/0037465 A1 | 2/2004 | Krause |
| 2004/0175043 A1 | 9/2004 | Lee |
| 2004/0243270 A1 | 12/2004 | Amirthalingam |
| 2004/0246510 A1 | 12/2004 | Jacobsen et al. |
| 2005/0004956 A1 | 1/2005 | Pourdeyhimi |

FOREIGN PATENT DOCUMENTS

| | | |
|---|---|---|
| DE | 34 13 558 C2 | 10/1985 |
| DE | 40 08 366 A1 | 9/1990 |
| DE | 19930154 A1 * | 1/2001 |
| EP | 160304 A2 * | 11/1985 |
| EP | 0 612 977 A2 | 8/1994 |
| EP | 703443 A1 * | 3/1996 |
| JP | 64001936 A * | 1/1989 |
| JP | 07243187 A * | 9/1995 |
| JP | 07311144 A * | 11/1995 |

* cited by examiner

MEASURING FIBER ORIENTATION BY DETECTING DISPERSION OF POLARIZED LIGHT

FIELD OF THE INVENTION

The present invention is directed to techniques of determining the fiber orientation in webs formed from non-woven materials and particularly to image-based measurements of the average the fiber orientation of paper using dispersion of linearly or plane-polarized light.

BACKGROUND OF THE INVENTION

In the manufacture of paper on continuous papermaking machines, a web of paper is formed from an aqueous suspension of fibers (stock) on a traveling mesh, papermaking fabric, or wire and water drains by gravity and suction through the fabric. The web is then transferred to the pressing section where more water is removed by pressure and vacuum. The web next enters the dryer section where steam heated dryers and hot air completes the drying process. The paper machine is, in essence, a water removal, system. Papermaking devices well known in the art are described for example in Handbook for Pulp & Paper Technologists 2nd ed., G. A. Smook, 1992, Angus Wilde Publications, Inc., and Pulp and Paper Manufacture Vol III (Papermaking and Paperboard Making), R. MacDonald, ed. 1970, McGraw Hill. Sheetmaking systems are further described, for example, in U.S. Pat. No. 5,539,634 to He, U.S. Pat. No. 5,022,966 to Hu, U.S. Pat. No. 4,982,334 to Balakrishnan, U.S. Pat. No. 4,786,817 to Boissevain et al., and U.S. Pat. No. 4,767,935 to Anderson et al.

In the art of modem high-speed papermaking, it is well known to continuously measure certain properties of the paper material in order to monitor the quality of the finished product. These on-line measurements often include fiber orientation (FO), basis weight, moisture content, and sheet caliper, i.e., thickness. The measurements can be used for controlling process variables with the goal of maintaining output quality and minimizing the quantity of product that must be rejected due to disturbances in the manufacturing process. The on-line sheet property measurements are often accomplished by scanning sensors that periodically traverse the sheet material from edge to edge.

Fiber orientation in papermaking refers to the preferential orientation of the individual fibers on the web. Because of flow patterns in the headbox and the jet impingement on the wire, fibers have a tendency to align in the machine direction (MD) versus other directions in the web. If all of the fibers in the web were perfectly distributed, the paper sheet would have the same properties in all directions. This is called an isotropic sheet and its fiber distribution can be plotted on a polar graph in the form of a circle.

If there are more fibers in one direction than in other directions the fibers are distributed non-uniformly and the sheet is anisotropic. As shown in FIG. 22, the anisotropic fiber distribution can be plotted on a polar graph as a symmetrical ellipse-like geometric 2. An anisotropic sheet has a fiber ratio greater than one and with higher fiber ratios the polar distribution tends to be in the shape of a figure eight. The fiber ratio (anisotropy) is defined as the ratio of maximum to minimum distribution, 90° apart. An isotropic sheet has a fiber ratio of one. The fiber angle α is defined as the angle of the major axis 6 of the ellipse 2 to the machine direction 4. The minor axis 8 is perpendicular to the major axis 6. FIG. 23 also illustrates the definitions of FO ratio (the ratio of max 3 to min 5) and FO angle of fiber distribution in a paper sheet. Fiber ratios can also be defined for other orthogonal directions, and it is common in papermaking to use the ratio of the fiber distribution in the machine direction 4 to the fiber distribution in the cross-machine direction 9.

Fiber orientation in formed webs can influence numerous properties of the final product. In particular, if the fiber orientation distribution is incorrect, then dimensional instability in the form of twist, curl, and skew will occur, and strength axes will not correspond to manufacture axes. This leads to defective products such as paper that jams in printers/copiers, packaging that jams in discrete item containers, and boxes which lean or collapse when stacked. By accurately measuring the fiber orientation on-line in the manufacturing process, it is possible to rectify problems in a timely manner either by manual intervention or by a fiber orientation control system.

Numerous techniques for measuring fiber orientation have been suggested some of which are based on the transmission of laser or maser spots from polarized or unpolarized light sources. The distortion of the spot in transmission through the web or the directional variation in intensity of reflection of the illuminated spot, specular or aspecular, is measured. Because the spot illumination area is relatively small, these techniques do not necessarily yield representative measurements for the sheet. Many of these indirect techniques that measure proxies of fiber orientation are based on the physical principle that fibers scatter more light across their alignment direction than along it.

For example, CA 2,012,351 to Karasikov et al. discloses a system for determining fiber orientation in a stationary or moving web of fibers wherein a small circular light spot is focused onto a first surface of the web thereby forming an ellipse-shaped spot on the opposite or second surface of the web. The elliptical light spot is focused onto an array of light-sensitive elements that are positioned parallel and at a predetermined distance on the second surface of the web. The fiber orientation is determined by evaluating the size, orientation and aspect ratio of the ellipse-shaped spot in the image.

U.S. Pat. No. 4,955,720 to Blecha et al. discloses an on-line method that illuminates one side of a moving sheet with a circular spot of coherent light and acquires a freeze-frame image of the transmitted spot on the opposite side. The fiber orientation angle is estimated from the shape of the transmitted spot, which is presumed to be elliptical.

Similarly, U.S. Patent No. Application 2003/0156293 to Kazuhiko et al. discloses a method that uses an unpolarized focused light beam to illuminate a circular spot on one side of a sheet and images the transmitted spot on the opposite side. Fiber orientation angle and anisotropy are estimated by approximating the transmitted spot shape with an ellipse.

All of the abovementioned methods illuminate the sheet with a circular spot of incident light and their measurement principle requires that the spot of excident transmitted light be elliptical in shape. In fact, the excident spot of transmitted light is elliptical in shape only if the fiber orientation distribution of the sheet has particular properties, such as being unimodal and being symmetric around its maximum. A unimodal distribution has a single maximum and a single minimum. In some instances, the fiber orientation distribution can be bimodal or multimodal, such that there are a plurality of maxima and a plurality of minima in the fiber orientation distribution. Moreover, even if the fiber orientation distribution is unimodal, the distribution of angles is not always symmetric around that maximum, in which case the excident light spot is not elliptical in shape. The abovementioned methods produce unreliable estimates of the fiber orientation angle and the fiber orientation anisotropy, if the fiber orientation distribution of the sheet is not unimodal or is not symmetric.

Multimodal or asymmetric distributions can arise, for example, in multi-ply paperboard, which is made by splicing together two or more separately formed sheets which have different fiber orientation distributions. They can also arise in single-ply sheets, as a result of local vortices in the jet from the headbox, or as a result of other structured differences in the flow field through the jet, especially when the slice channel of the headbox is equipped with vanes separating the flow into layers.

An asymmetric distribution can be unimodal or multimodal, and a multimodal distribution can be symmetric or asymmetric. Detection and quantification of asymmetry or multimodality of the fiber orientation distribution is important in monitoring the process and diagnosing defects in the manufactured product.

DE 3,413,558 to Hartig describes a technique that employs polarized laser light to illuminate a laser spot on one side of a sheet. Four photodiodes are positioned at the nominal edges of the expected excident spot position along x and y axes on the opposite side. The fiber orientation and anisotropy are determined from the ratio of transmitted intensities summed on each axis. As in the above systems, the Hartig device also measures the total or average fiber orientation in the sheet.

U.S. Pat. No. 5,475,233 to Fukuoka et al., U.S. Pat. No. 5,640,244 to Hellstrom et al., and U.S. Pat. No. 6,643,022 to Komppa disclose various methods in which laser light is obliquely directed onto a sheet and the intensity of aspecularly reflected laser light is measured at various directions and inclination angles. The surface fiber orientation determination is based on the differences in the illumination reflectivity when measured from a number of directions. The methods disclosed differ to some extent in the geometries of the illuminations employed.

Due to the low incidence angles used for illumination in these methods, their measurements of reflected light provide information about the fiber orientation distribution in a thin layer at the surface of the sheet. The measurement predominantly represents the first layer of fibers, with reflections mostly occurring at the fiber surfaces facing the sheet surface, and typically lying within 20 microns of the sheet surface. These measurements therefore provide little or no information concerning fiber orientation deeper within the sheet, which can be of great importance in papermaking. Moreover, they can produce biased results if the sheet surface is unconsolidated such that there are fibers partly protruding from the sheet, or if the sheet surface roughness has high amplitude at millimeter scales. They are also sensitive to small changes in the plane of the paper being measured, both in position with respect to the measuring device and in the geometrical relation of the paper plane and the various directions used in illumination and detection of light.

Image analysis is a standard laboratory technique for fiber orientation measurements of paper whereby transmission images of stationary sheets taken from flatbed scanners or similar devices are analyzed. Since paper strongly scatters light, the samples usually must be peeled into layers for transmission or reflection imaging to be feasible. The layers typically are very thin and weigh just a few grams per square meter (gsm). This laboratory process is labor-intensive and not applicable to on-line measurements of moving webs.

Therefore, despite the asserted advantages associated with these fiber orientation measurement systems, none of these apparatuses affords a simple, robust, and accurate device for on-line fiber orientation measurements of a moving web or sheet made of nonwoven components.

SUMMARY OF THE INVENTION

The present invention is based in part on the recognition that the fiber orientation along the entire depth or thickness of a fibrous, non-opaque web can be measured by analyzing the dispersion of linearly or plane-polarized collimated light beams that are transmitted through the web. The total fiber orientation calculations are based, in part, on the principle that the degree of dispersion of a plane-polarized beam is related to the difference between its plane of polarization and the average orientation of fibers in its path. In addition, the difference in dispersion of beams having different polarization planes is also characteristic of the degree of anisotropy of the fibrous web.

In one aspect, the invention is directed to a method for measuring the fiber orientation of a moving web that includes the steps of:

(a) illuminating essentially simultaneously at least four light spots on a first side of the web with at least four plane-polarized incident light beams having different polarization characteristics, wherein each of the at least four plane-polarized light beams is incident substantially perpendicular to the web surface and is transmitted through the web to produce at least four corresponding transmitted excident light spots on a second side of the web that is opposite to the first side;

(b) for each of the at least four plane-polarized light beams, measuring the dispersion of the excident light spot along at least one linear section which is at a known angle relative to the plane of polarization of the corresponding plane-polarized incident light beam, wherein at least one such linear section lies substantially across the center of the transmitted excident light spot and extends substantially across the width of the transmitted excident light spot;

(c) calculating variations, if any, in the dispersion of the transmitted excident light spot for the at least four plane-polarized light beams; and (d) estimating the fiber orientation of the web from the variations.

In another aspect, the invention is directed to a system for measuring the fiber orientation of a web that includes:

means for illuminating at least four light spots essentially simultaneously on a first side of the web with at least four plane-polarized incident light beams having different polarization characteristics, wherein each of the at least four plane-polarized light beams is incident substantially perpendicular to the web surface and is transmitted through the web to produce at least four corresponding transmitted excident light spots on a second side of the web that is opposite to the first side;

image obtaining means for obtaining at least one image of an illuminated area on the second side of the web wherein the illuminated area contains the transmitted excident light spots from the at least four incident light beams control means associated with each of the at least four plane-polarized light beams for measuring the dispersion of the excident light spot along at least one linear section which is at a known angle relative to the plane of polarization of the corresponding plane-polarized incident light beam, wherein at least one such linear section lies substantially across the center of the transmitted excident light spot and extends substantially across the width of the transmitted excident light spot;

means for calculating variations, if any, in the dispersion of the transmitted excident light spot for the at least four plane-polarized light beams; and means for estimating the fiber orientation of the web from the variations.

The image-based measurement technique is particularly suited for incorporation into a continuous web production process, such as for making paper, where the fiber orientation of the moving web is monitored. Images of the moving web can be ascertained at one or more fixed positions relative to the moving web either in the machine direction or cross direction. Images can also be ascertained as an image detector scans back-and-forth typically in the cross direction across the moving web. For example, the image detector can be mounted on a traversing sensor platform so that the full width of the web is sequentially measured. The invention can also be employed as an array of devices, each measuring part of the web, such that the fiber orientation of substantially the entire web width is measured simultaneously.

The present invention for measuring fiber orientation simultaneously illuminates a surface of the web with a plurality plane-polarized light beams. As a corollary, the inventive technique exhibits important advantages over the prior art, including, for instance: (i) it does not require moving parts, such as rotating polarizers or rotating detectors, so that its construction is simpler and more robust; (ii) it is not vulnerable to fast variations in the anisotropy of the web, so that the measurement results are more reliable; (iii) it provides a higher resolution measurement in the time domain; (iv) it is not sensitive to positional or geometric changes in the plane of the measured sheet relative to the measuring device; and (v) in the case of a scanning measurement, it can provide higher resolution measurements in the position domain.

The present invention also differs from many conventional methods of measuring fiber orientation that rely on imaging transmitted light since the invention is not based on measuring the geometric distortion of a known spot shape on transmission through a sheet or web. Indeed, the invention does not require that the illumination be a well-defined spot or that the illuminated area exhibit any particular shape, circular or otherwise. It is advantageous in some instances with the present invention, however, for each spot to be of approximately square or rectangular section, with the polarization plane of the light being parallel to a side of the spot.

Furthermore, the present invention does not endeavor to estimate the fiber orientation of a web by measuring the shape of the excident illumination or by identifying intensity contours or other proxies that are correlated to the shape of the excident illumination. Instead, with the present invention, fiber orientation is based on measurement of the dispersions of transmitted plane-polarized light.

DETAILED DESCRIPTION OF THE PREFERRED EMBODIMENTS

The present invention relates to methods and devices for calculating the fiber orientation in nonwoven materials especially where the material is in the form of a moving web, film or sheet. The fiber orientation of the whole thickness of the web of the web can be measured. The fiber orientation measurements can be expressed as one or more different parameters that are used in controlling the papermaking process and/or characterizing the properties of the product. The parameters include, for instance: average fiber orientation angle and fiber orientation anisotropy index. In addition, the fiber orientation measurements from both sides of the web can yield information regarding curl and twist deformations of the web, e.g., paper.

While the invention will be illustrated in measuring fiber orientation of paper, it is understood that the invention can be employed to analyze fiber orientation in a variety of products that are formed from non-woven fibrous materials including, for example, paperboard, tissue and the like. In addition, the invention has applicability outside products that are derived from cellulose. For instance, the measurement techniques can be applied in the manufacture of glass fiber sheets in which the control of fiber orientation distributions is also critical.

Figure 1:
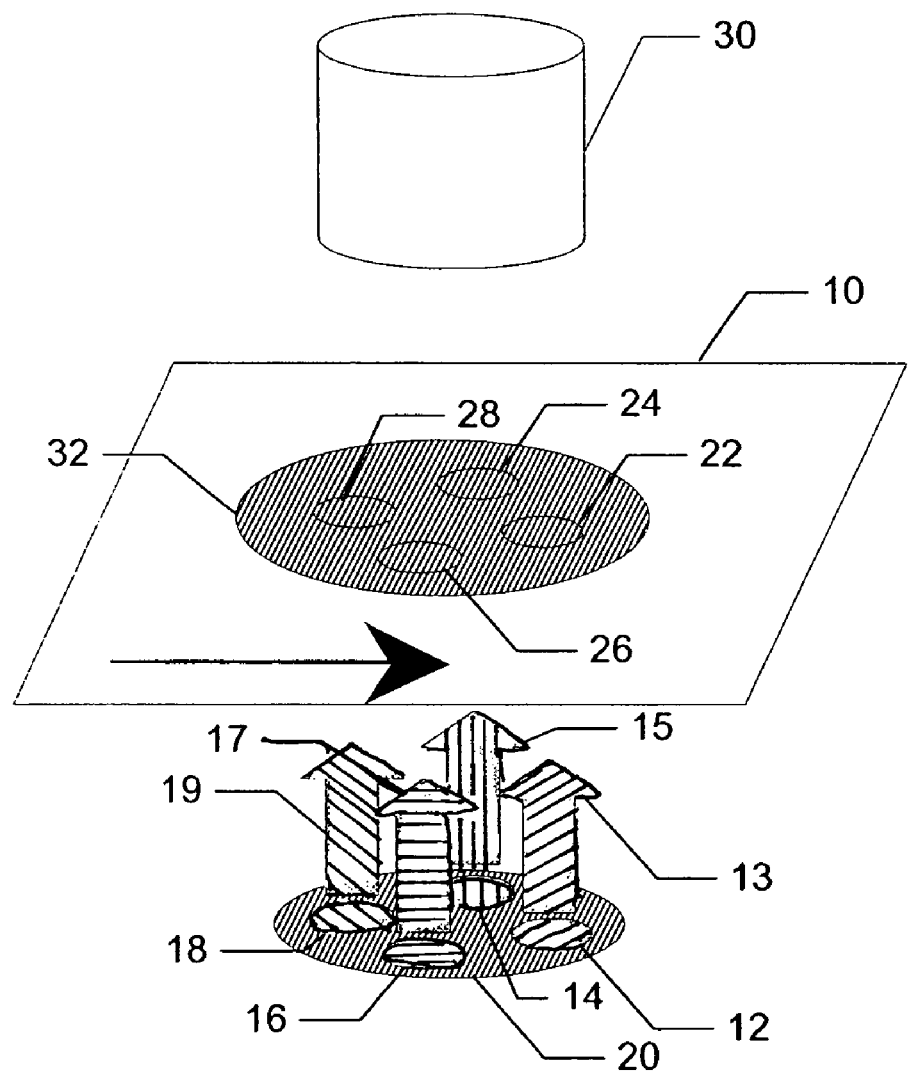
FIG. 1 illustrates an apparatus for on-line image-based measurement of average fiber orientation using dispersion of polarized light.

As shown in FIG. 1, an on-line apparatus for measuring fiber orientation of a moving web or sheet of paper 10 is positioned between a light source array 20 and an imaging device 30, that can be equipped with appropriate optics, e.g., lenses, to focus the light that is transmitted through the web. Ultraviolet (UV), visible, and near-infrared (NIR) radiation are particularly suited for the analysis and a preferred light source is monochrome light, e.g., laser, or nearly monochrome, e.g., LED, with wavelengths between 0.1 and 5.0 microns. However, rich illumination can also be used, in which case it is advantageous to employ a narrow-band filter for imaging. The typical wavelength range is from 100 nm to 5000 nm and preferably the range is from 300 nm to 2000 nm. If the web contains fluorescent agents, it is preferred that the illumination has no power or only insignificant power in the fluorescent excitation band; alternatively, an imaging filter can be used to block the fluorescent emission band from the illumination.

The light source array 20 generates at least four linearly or plane-polarized collimated light beams 13, 15, 17, and 19 of light that are directed onto one side, e.g., lower surface, of the web 10 at a substantially normal incidence such that each beam illuminates a unique spot. The term "spot" or "incident spot" refers to an area on the surface of the web where a collimated light beam is incident and transmitted. The term "excident spot" refers to the corresponding area on the opposite surface of web where the collimated light beam is excident. When only four light beams are employed, the light beams 13, 15, 17, and 19 are polarized in different planes of polarization. When more than four light beams are employed, a minimum of four beams that are plane-polarized at four different planes of polarization are used. Polarizing filters 12, 14, 16, and 18 can be employed to produce the four plane-polarized beams 13, 15, 17, and 19, respectively, and the intensities of the beams are preferably the same. In this example, as shown in FIG. 1, the four directions of polarization are approximately 45 degrees apart. The intensities of the four light beams should be high enough that the incident beams transmit or penetrate through the thickness of the web 10 to illuminate the upper surface of the web 10 for images of the image area 32 to be focused into the imaging device 30, e.g., camera.

The width of each collimated light beam 13, 15, 17 or 19 should be such that the beam is partly dispersed by scattering in the fibrous web 10. The term "dispersion" as used herein refers to the scattering of a collimated beam as it passes through a scattering medium. As further described herein, the fiber orientation angle that is measured is defined as the angle of the plane of polarization in which the variation in dispersion across specific sections of the transmitted light is greatest. The degree of orientation is measured from the variation in maximum and minimum dispersions.

For visible and near-visible wavelengths in paper webs, the preferred incident spot size is from 50 microns to 1000 microns in width. For a uniform beam whose width greatly exceeds the web thickness, the central part of the excident spot will also be uniform, and dispersion effects will be measurable over an annulus around the center, where the width of the annulus will be a few times the sheet thickness.

The light beam size is preferably small enough so that dispersion effects are discerned over the whole of the excident spot on the opposite side of the web. If the fiber orientation is to be measured for webs of significantly different thicknesses, it may be advantageous to provide masks containing apertures of suitable sizes so that the spot size can be optimized for a plurality operating ranges. A calibration step, as further described herein, must be performed separately with each mask.

As shown in FIG. 1, the four light beams 13, 15, 17, and 19 create four illumination excident spots 22, 24, 26, and 28, respectively, on the upper surface of the web 10. The defined shape associated with each light beam is preferably symmetric with at least one axis of symmetry or a center of symmetry; most preferably, the defined shape is circular or rectangular, or forms a line segment. The defined shape for each beam has at least one width that is preferably less than 10 times the web thickness. The illumination intensity within the area of the defined shape is preferably symmetric and most preferably essentially uniform.

The image scale of the image area 32 must be high enough to allow sections across the excident spots to be detected at sufficient resolution for the dispersion to be reliably estimated. Thus, the part of the excident spot with nonuniform but detectable brightness should be at least several pixels wide. For instance, when employing a small illuminating beam such that the dispersion affects the whole beam, the excident spot is preferably more than 20 pixels wide across a section to be measured. In practice, the intensity variation will typically occur over more than 100 microns at each nominal edge of the spot, so that a field image scale of 10 microns per pixel is adequate.

While a plurality of round spots, each with a different plane of polarization, could be used, this configuration would require good alignment between illumination and imaging device 30. Therefore, rectangular or piecewise rectangular spots are preferable, especially those that are formed from elongated rectangles or lines. In this case, alignment is less critical since the measurement section is constrained in only one axis. Thus, a plurality of sections can be taken, and averages or other characteristic aggregated measurements can be formed. Rectangular or linear illuminated spots can be formed using suitable masks and lenses, and this also allows combinations into piecewise rectangular shapes such as cruciform or L shapes as further described herein.

To optimize the information content in the image, it may be advantageous to ensure that all the light beams have similar intensities. Moderate differences in intensity, or nonuniformity in intensity distribution, can be compensated by measuring spot dispersion in calibration images. However, the effects of saturated pixels or detector blooming cannot be compensated and should be avoided. This can be achieved by varying the illuminator power or the image exposure time so that no pixels become saturated. Controlling individual beam intensity ensures that enough dynamic range exists for each spot.

The excident light that emerges on the upper surface of the web 10 is partly or mostly depolarized, depending on the thickness of the web. For fibrous webs such as paper, the fibers are aligned randomly but not isotropically, i.e., not all alignment angles are statistically equivalent. As a corollary, the web's scattering behavior with respect to polarized light depends on the plane of polarization of the light: if the plane of polarization coincides with the dominant fiber alignment direction, scattering is less than the case where plane of polarization is perpendicular to the dominant fiber alignment.

Conventional lenses can be employed with the imaging device 30, e.g., camera, when the moving web 10 is stable so that its distance from the imaging device 30 is relatively constant which is the case when the web 10 is adequately supported. Optimal image scales can be obtained using macro or high magnification optics. For example, if aerodynamic effects cause the moving web 10 to flutter or otherwise shift its vertical position relative to the imaging device 30, a telecentric lens system that creates a large depth of field can be used so that fluctuations of the web 10 relative to the camera results in no change in image size. Telecentric designs also facilitate macro scales, such as 1:1.

Figure 2:
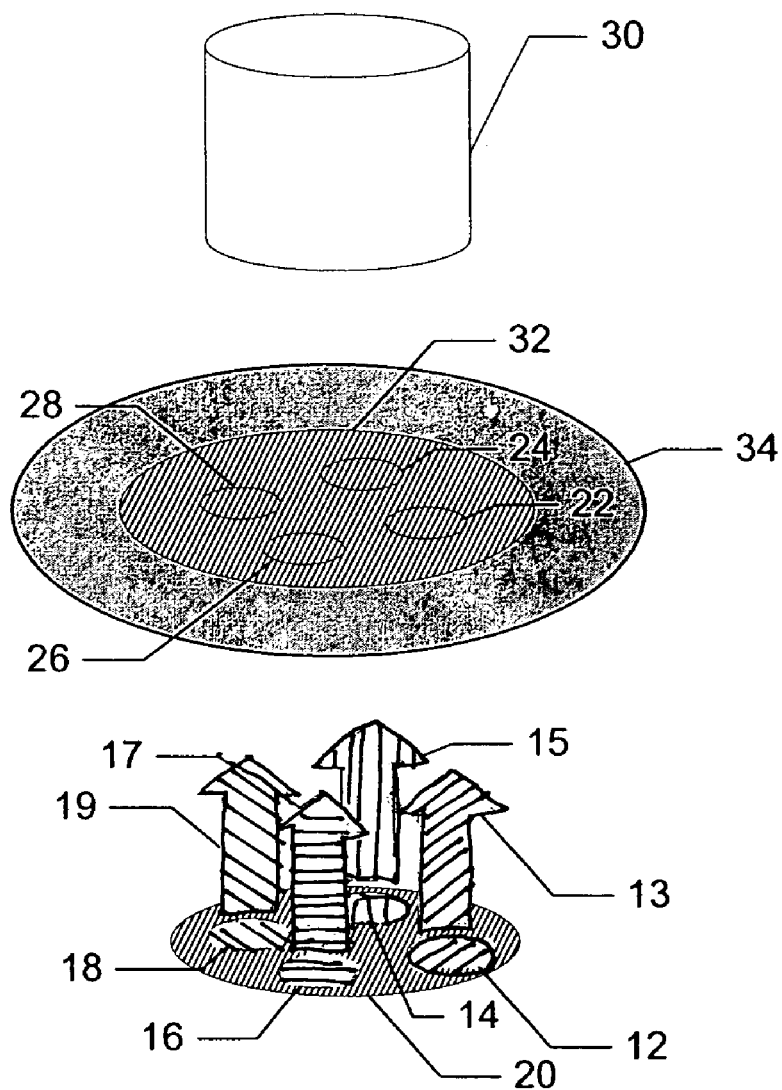
FIG. 2 illustrates calibration of the on-line image-based measurement apparatus.

As further described herein, measuring the fiber orientation of a web of nonwoven material entails calculating variations, if any, in the dispersion of the transmitted excident light spot for the at least four plane-polarized light beams. In this regard, the system for measuring the fiber orientation is preferably calibrated using an isotropic and an anisotropic reference material. As shown in FIG. 2, during a first calibration phase of the on-line image-based fiber orientation apparatus, a uniform isotropic reference material 34 of known transmittance is placed substantially in the same plane as occupied by the web or sheet during measurement as depicted in FIG. 1. The reference 34 is illuminated during calibration in essentially the same way as the sheet is illuminated during measurement. The illuminated areas 32 of the reference 34 are imaged on the other surface, and the light dispersions are measured. The intensities and dispersions of light measured during calibration are used to characterize differences in illumination intensity or distribution in the illuminated areas, and thus to normalize the calculations based on dispersion measurements. With this normalization step, it is possible to make reliable measurements even with beams which are not uniform in intensity across the illuminated spots. The isotropic reference 34 in the case of visible light may be, for instance, a sheet of opal glass, whose transmittance is known at least in the areas illuminated by the light source array 20. Transmittance at any point through the reference material 34 most preferably is the same for all planes of polarization.

Similarly, during a second calibration phase also shown in FIG. 2, one or more uniform anisotropic references 34 of known anisotropy are sequentially placed substantially in the same plane as occupied by the sheet during measurement. Each reference 34 is illuminated during calibration in essentially the same way as the sheet is illuminated during measurement. The illuminated areas 32 of each reference are imaged on the other surface, and the light dispersions are measured. Optionally, one or more anisotropic references may be rotated to plural known orientation angles and the light dispersions measured at each orientation. A chosen proxy variable is evaluated using the transmitted light dispersions measured for the anisotropic references 34, and a correlation is formed between the evaluated proxy variable and the known anisotropies of the references. The anisotropic references may be, for instance, formed mats of fibers of dimension similar to the nominal dimensions of fibers in a measured sheet. The references may also be uniform sheets of paper of known anisotropy. The anisotropy of each reference should be known, for instance, as the distribution of fiber angles within the reference.

Figure 3A:
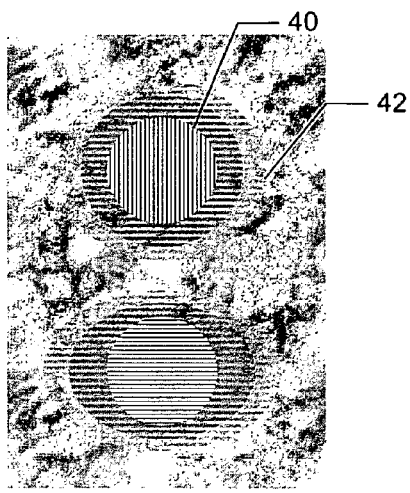
FIGS. 3A, 4A and 5A each depicts polarized incident spots with uniform intensity on the illumination side of a web and excident or transmitted spots of dispersed intensity on the opposite side.

The following examples illustrate the principles of fiber orientation measurement using different shaped light beams. In the first example, as shown in FIG. 3A, light beams shaped as symmetric round spots 40, such as circles or ellipses, are employed. The spots 40 represent polarized light that has a uniform intensity on the illumination side of the web; two incident polarized spots having orthogonal planes of polarization are shown. The excident or transmitted spots 42 that appear on the opposite side of the web have dispersed intensity contours. Intensity sections are taken across the transmitted spots in a plurality of directions approximately crossing the spot's center, using pixels in suitable locations, by interpolating from nearby pixels, or by weighted averaging of nearby pixels. One direction should match the plane of polarization, and another should be orthogonal to it. Sections in other directions can also be evaluated.

Figure 3B:
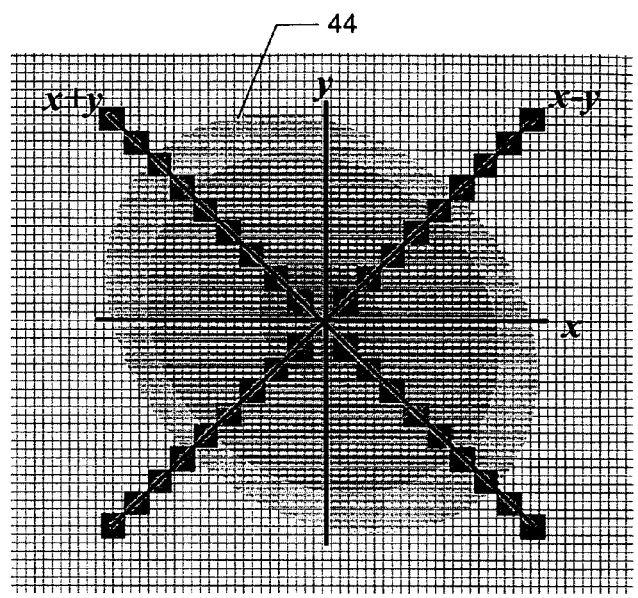
FIGS. 3B, 4B, and 5B each is an image of a dispersed transmitted spot showing the contours of the intensity of the excident light.
Figure 3C:
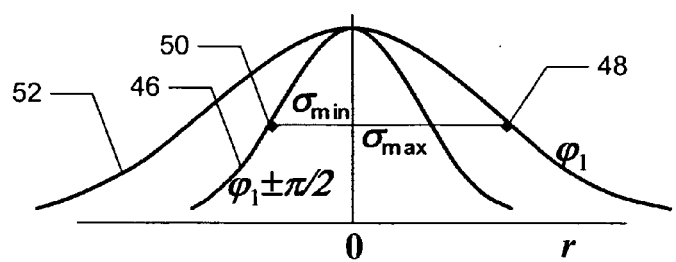
FIGS. 3C and 5C each is a graph of intensity curves along chosen sections through the excident light.

FIG. 3B is an image of a dispersed spot which shows the contours of the intensity of the excident light. Each square in the image represents a pixel/intensity section through the transmitted spot. The x+y line (or linear section) is the dispersed intensity contour as measured along an orthogonal of the polarization plane and the x−y line (or linear section) is the dispersed intensity contour as measured along the polarization plane. Finally, FIG. 3C shows a graph of the intensity curves along two chosen sections through the excident light as measured from r, the radius from the spot center. In this case, intensity curves are measured for the transmitted light at polarization angles of $\phi_i$ (curve 52) which correspond to the x+y line of FIG. 3B and $\phi_1 \pm \pi/2$ (curve 46) which correspond to the x−y line. $\sigma_{max}$ is the maximum dispersion distance as measured from the spot center to point 48 and $\sigma_{min}$ is the minimum dispersion as measured from the spot center to point 50.

Figure 4A:
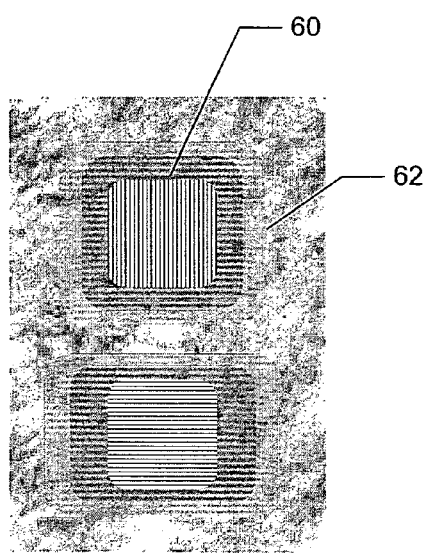

In the next example as shown in FIG. 4A, light beams whose cross-section is essentially rectangular or square shaped are employed. The polarized spots 60 represent polarized light that has a uniform intensity on the illumination side of the web; two incident polarized spots having orthogonal planes of polarization are shown. The excident or transmitted spots 62 that appear on the opposite side of the web have dispersed intensity contours. By using spots whose cross-section is essentially rectangular or square, the sections need not cross very close to the center of the spot. This allows the detector and the beam to be less precisely aligned. A plurality of sections can be taken around the nominal center. A representative section can be chosen, or formed from more than one section by averaging. It is advantageous for the illumination intensity to be essentially the same across sections near the center of the incident spot and to be parallel to its sides.

Figure 4B:
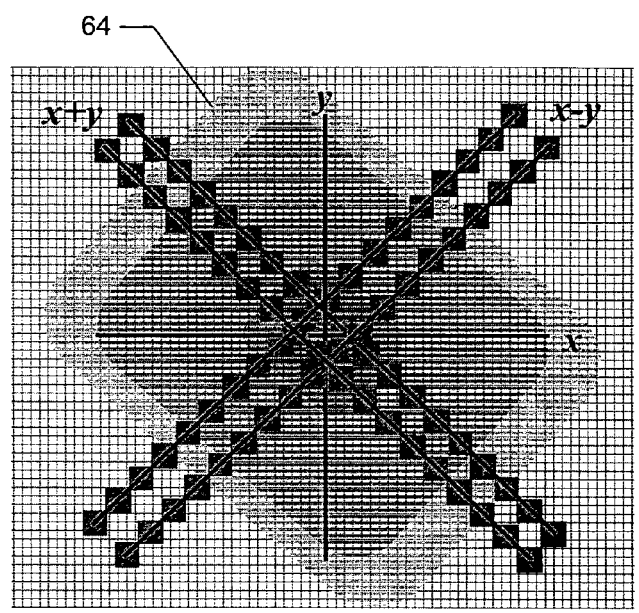

FIG. 4B is an image of a dispersed spot which shows the contours of the intensity of the excident light. The x+y lines (or linear sections) are the dispersed intensity contours as measured along the polarization plane and the x−y lines (or linear sections) are the dispersed intensity contours as measured along an orthogonal of the polarization plane. Finally, a representative graph of the intensity curves along two chosen sections through the excident light as measured from r, the radius from the spot center is shown in FIG. 3C.

Finally, light beams with linear areas can be used to illuminate the web with polarized light. In this case, one or more sections can be measured across each line. This further relaxes the need for accurate alignment of the detector. Sections can be taken at plural locations in a line, preferably in directions which are substantially perpendicular to the line. A representative section can be chosen, or formed from more than one section by averaging or other techniques. It is advantageous for the illumination intensity to be essentially the same along the part of the line where sections are to be taken.

Figure 5A:
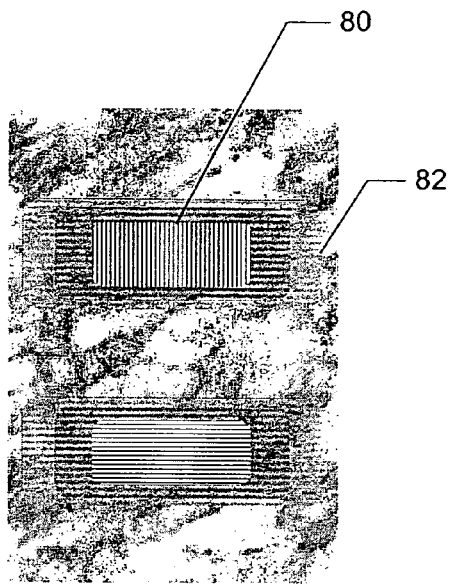
Figure 5B:
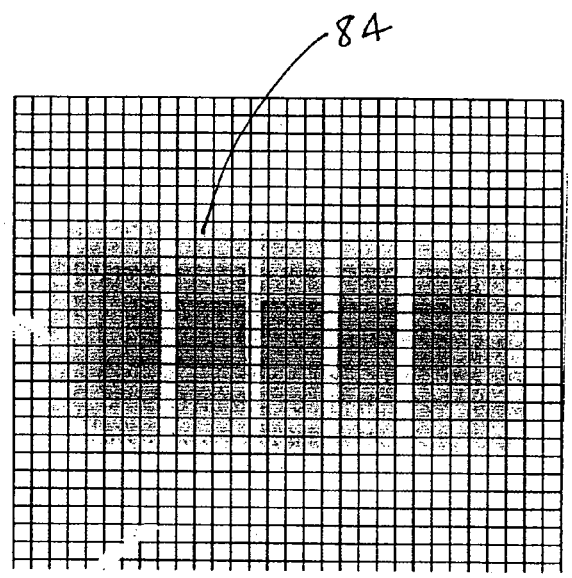
Figure 5C:
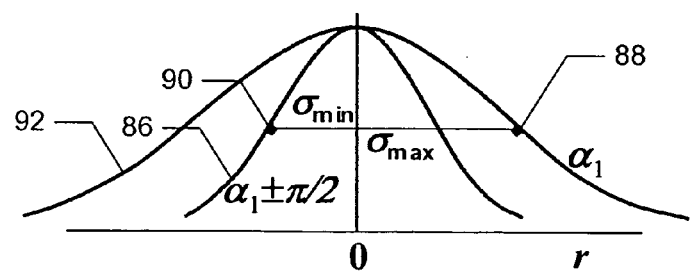

As shown in FIG. 5A, the polarized spots 80 represent polarized light that has a uniform intensity on the illumination side of the web; two incident polarized spots having orthogonal planes of polarization are shown. The excident or transmitted spots 82 that appear on the opposite side of the web have dispersed intensity contours. FIG. 5B is an image 84 of a dispersed line which shows the contours of the intensity of the excident light. Finally, FIG. 5C shows a graph of the intensity curves along two chosen sections through the excident light as measured from r, the radius from the spot center. In this case, intensity curves are measured for the transmitted light at polarization angles of $\phi_i$ (curve 92) and $\phi_1 \pm \pi/2$ (curve 86). $\sigma_{max}$ is the maximum dispersion distance as measured from the spot center to point 88 and $\sigma_{min}$ is the minimum dispersion as measured from the spot center to point 90.

These intensity contours or sections can be measured without using a polarization-sensitive detector. It should be noted that the excident light is partly or mostly depolarized, depending on the thickness of the paper. However, paper is a fibrous web whose fibers are aligned randomly but not isotropically (not all alignment angles are statistically equivalent). Thus, its scattering behavior for polarized light depends on the plane of polarization of the light: if the plane of polarization coincides with the dominant fiber alignment direction, then scattering is less than if the plane of polarization is perpendicular to the dominant fiber alignment.

In thick sheets for which a relatively short wavelength of light is used in illuminating the polarized spots, the light is essentially completely depolarized after penetrating only part of the way through the sheet. In this case, the variations in the dispersions of the excident light spots having different planes of polarization will be largely determined by the orientation of fibers in the layers closer to the illuminated side of the sheet. The dispersions of the excident light spots will also be affected by the fiber orientation in layers lying closer to the excident side of the sheet, but this effect will not depend on the plane of polarization of the incident spots, and will therefore be the same for all spots.

Thus, in another aspect of the invention, by employing more than one wavelength of light in making the measurements, it is possible to distinguish between the fiber orientations in different layers of a thick sheet. For instance, variations in dispersion of light spots having different planes of polarization using light of a relatively short wavelength will largely be determined by the fiber orientation of the surface layers on the illuminated side, while variations in dispersion of light spots having different planes of polarization using light of a relatively long wavelength will be determined by the fiber orientation of surface and subsurface layers. The fiber orientation of the surface and subsurface layers can hence be inferred from the measurements at the two wavelengths. As is apparent, by using a greater plurality of different wavelengths, it is possible to infer the fiber orientation at more than two layers of the sheet. Polarized monochrome light of different wavelengths can be used to illuminate spots independently, either sequentially or simultaneously. Alternatively, by illuminating spots with polarized light which has a rich spectrum or contains multiple wavelength bands, the different wavelength bands of interest can be distinguished by the imaging devices. For instance, plural imaging devices responsive to different wavelength bands can be used, or a single imaging device can be used with filters which select the wavelength bands of interest. Rich spectrum sources include incandescent filaments such as Tungsten-Halogen lamps and arc discharges such as filtered Xenon lamps. Multiple band sources include fluorescent lamps employing tri-band phosphors with Mercury vapor discharges.

Similarly, in yet another aspect of the invention, by illuminating a sheet on both sides, either sequentially or simultaneously, with light spots having different planes of polarization and making measurements of the dispersion of the corresponding excident light spots, it is possible to infer the difference in the fiber orientation between the two sides of the sheet.

The present invention does not rely on measurement of intensity contours, but on the variation in measured intensity along selected linear sections. Preferably, for light with a given plane of polarization one section coincides with the polarization plane, and another is perpendicular. As further described herein, by using separate light beams with different planes of polarization, the corresponding dispersions reveal the scattering power of the sheet in-polarization-plane and across-polarization-plane for different planes of polarization. If the nonwoven web is colored paper, scattering may be accompanied by absorption, which attenuates the transmitted light for all planes of polarization. However, absorption amplifies the difference between polarization planes, since more strongly scattered light has a longer optical path for transmission.

Figure 6A:
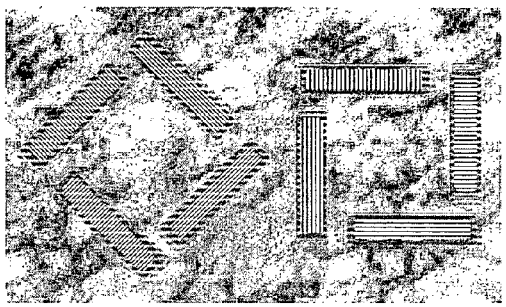
FIG. 6A depicts illumination on the web that includes an arrangement using pairs of lines of polarized light with four planes of polarization.
Figure 6B:
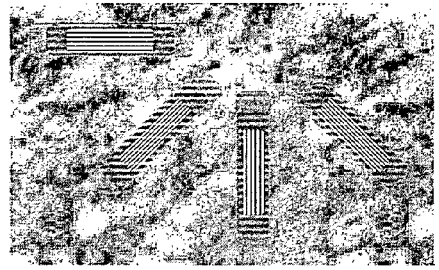
FIG. 6B depicts illumination on the web that includes an arrangement using single lines of polarized light with four planes of polarization.
Figure 6C:
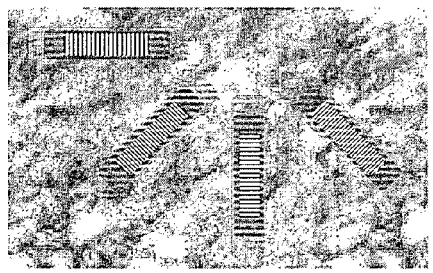
FIG. 6C depicts illumination on the web that includes an arrangement using single lines of polarized light with four planes of polarization.

Besides the polarized spot and line-shaped light beams configurations illustrated above, other exemplary light beam arrangements can be employed to illuminate a web. FIG. 6A illustrates two pairs of lines of polarized light with four planes of polarization. One line of each pair is parallel to and the other perpendicular to their plane of polarization. The polarized light has a uniform intensity on the illumination side of the web while the excident or transmitted spots that appear on the opposite side of the web have dispersed intensity contours. FIG. 6B illustrates single lines of polarized light with four planes of polarization, with each line axis parallel to its plane of polarization. FIG. 6C illustrates single lines of polarized light with four planes of polarization, with each line axis perpendicular to its plane of polarization.

Figure 6D:
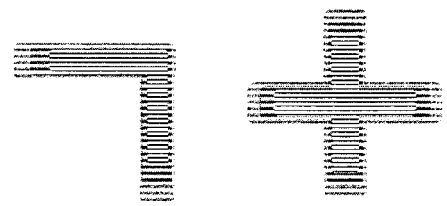
FIG. 6D illustrates that line pairs or larger multiples of lines sharing the same polarization plane can be generated as overlapping figures from a common polarized light source.
Figure 6E:
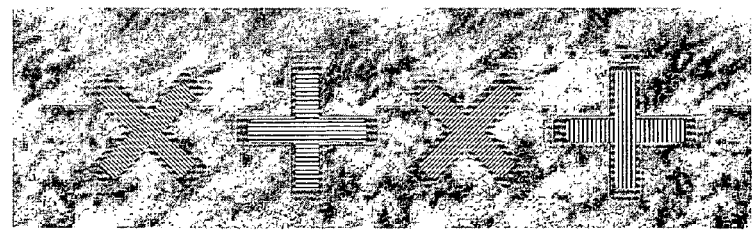
FIG. 6E depicts illumination on the web that includes an arrangement using shapes forming overlapping line pairs of polarized light with four planes of polarization.

As depicted in FIG. 6D, line pairs or larger multiples of lines sharing the same polarization plane may be generated as overlapping figures from a common polarized light source by means of suitable optical elements, such as lenses, shaped masks, and the like. In this case, the measured sections are not taken too close to the point of intersection of the lines. FIG. 6E illustrates shapes forming overlapping line pairs of polarized light with four planes of polarization. One line of each pair is parallel to and the other perpendicular to their plane of polarization.

A preferred method of calculating the fiber orientation angle ($\alpha$) is to first determine the maximum dispersion ($\sigma_{max}$) and minimum dispersion ($\sigma_{mix}$) for each of the at least four plane-polarized light beams using spot illumination wherein the transmitted intensities along sections parallel to and orthogonal to the polarization plane of each spot are measured. Preferably, the dispersions are normalized using dispersions of an isotropic reference measured during calibration.

Alternatively, instead of spot illumination, line illumination is employed with a line parallel to and a line perpendicular to the polarization plane wherein the transmitted intensities along sections orthogonal to each line axis are measured. A representative graph of the transmitted intensity as measured along the radius (r) of a section of a spot or line at polarization angles $\phi_1$ and $\phi_{1\pm}\pi/2$ is shown in FIG. 3C.

Figure 7:
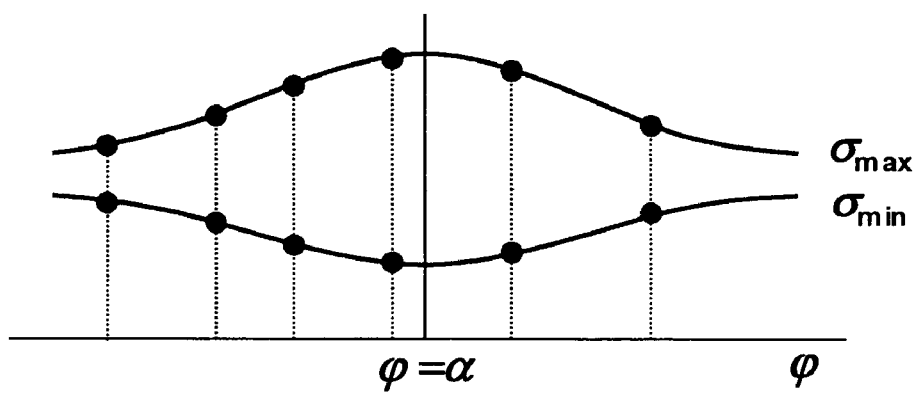
FIG. 7 is a plot of maximum dispersion and minimum dispersion at each plane of polarization where the data is connected by smooth curves.

The polarization plane corresponding to the highest ratio of or the greatest difference between the maximum and minimum dispersion can be estimated by interpolation or fitting, or by selecting among measurements, etc. The angle of this polarization plane is the measured fiber orientation angle. For example, FIG. 7 is a plot of the maximum dispersion and the minimum dispersion respectively measured in the plane of polarization and orthogonal to that plane from a plurality of spots illuminated with different planes of polarization ($\phi$). Smooth curves have been drawn through the maximum dispersions and minimum dispersions for different polarization planes in the Figure. From this graph, the ratio of the maximum to minimum dispersion for various planes of polarization can be readily ascertained by interpolation or fitting. As shown in FIG. 7, the angle ($\phi$) of the polarization plane with the highest ratio is the measured fiber orientation angle ($\alpha$).

Alternatively, the fiber orientation angle can be estimated using only the maximum dispersions or only the minimum dispersions measured from a plurality of spots having different planes of polarization. For example, if the dispersion is measured for each spot only in the plane of polarization of the spot, then only the maximum dispersions $\sigma_{max}$ of FIG. 7 are measured. In this case, the fiber orientation angle can be estimated as the plane of polarization corresponding to the maximum of these maxima, which can readily be ascertained by interpolation or fitting. In a similar way, if only the minimum dispersions $\sigma_{min}$ are measured, then the fiber orientation angle can be estimated as the plane of polarization corresponding to the minimum of these minima.

Figure 8:
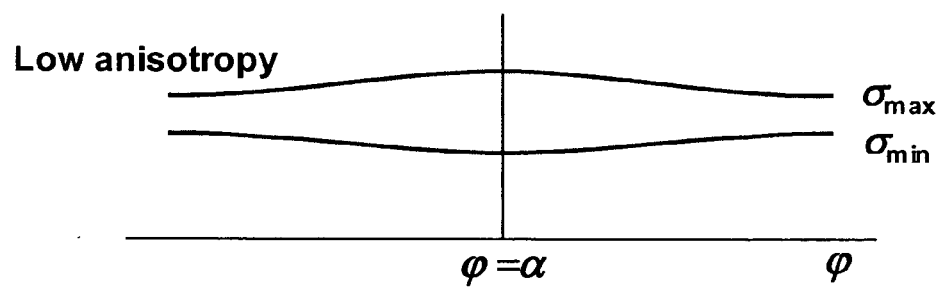
FIGS. 8, 9, and 10 are plots of maximum dispersion and minimum dispersion vs. plane of polarization which depict low, moderate, and high anisotropy, respectively.
Figure 9:
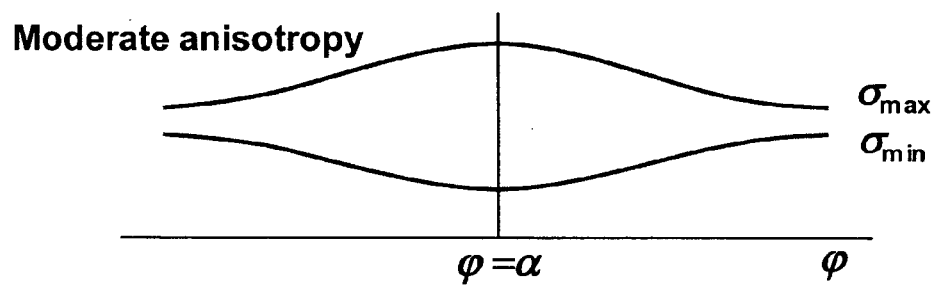
Figure 10:
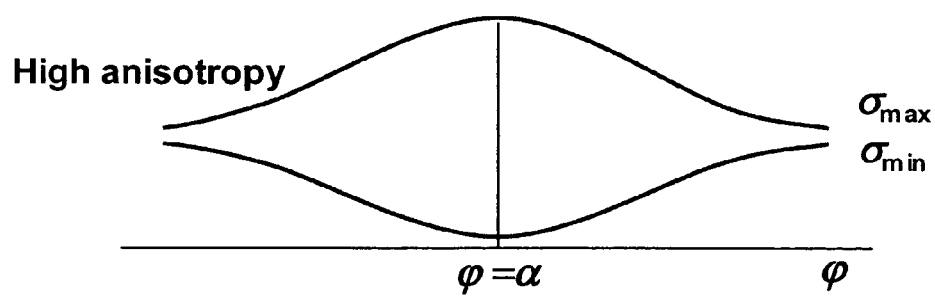

FIGS. 8, 9, and 10 are representative plots of maximum dispersion and minimum dispersion vs. plane of polarization that are characteristic of the different levels of anisotropy in a web ranging from low, moderate, to high anisotropy. As is apparent, the ratio of maximum dispersion to minimum dispersion is most pronounced where there is high anisotropy.

The degree to which fibers are aligned with the dominant fiber orientation direction can be characterized as a fiber orientation index or fiber orientation anisotropy. Numerous methods exist for measuring fiber orientation index or fiber orientation anisotropy, including measurements based on ultrasound propagation, image analysis, and the like. In general, high anisotropy values indicate a strongly oriented sheet, while low anisotropy values indicate a sheet in which the fiber directions are more uniformly distributed.

In another aspect of the invention, the fiber orientation index of a moving web or sheet can also be derived by evaluating a proxy variable (P) from measured dispersions of the transmitted excident light spots and estimating the fiber orientation of the web from the proxy variable with a known correlation. Any of several proxy variables can be used as correlates of anisotropy or fiber orientation index, including for example: (i) the ratio of the largest dispersion in the plane of polarization to the smallest dispersion in the plane of polarization, (ii) the ratio of the largest dispersion perpendicular to the plane of polarization to the smallest dispersion perpendicular to the plane of polarization, (iii) the ratio of the largest dispersion in the plane of polarization for any spot to the smallest dispersion perpendicular to the plane of polarization for any spot, (iv) the largest ratio of the dispersion in the plane of polarization to the dispersion perpendicular to the plane of polarization for the same spot, (v) the smallest ratio of the dispersion in the plane of polarization to the dispersion perpendicular to the plane of polarization for the same spot. As is apparent, the proxy variable ratios could be transformed without changing their utility in forming the correlations. For instance, a correlation formed using the inverse of a ratio is equivalent to a correlation formed using the ratio itself.

A method of developing a correlation between a proxy variable and the anisotropy or fiber orientation index is through a calibration procedure similar to that described above. In this case, two or more substantially planar anisotropic translucent reference materials with known anisotropies are used. For each reference material, at least four light spots are illuminated essentially simultaneously on one side of the reference material with at least four plane-polarized incident light beams having unique polarization characteristics. The light beams are preferably substantially perpendicular to the reference material surface and are transmitted through the reference material to produce at least four corresponding transmitted excident light spots on the opposite side of the reference material.

Thereafter, for each of the at least four plane-polarized light beams, the dispersion of the excident light spot along at least one linear section which is at a known angle relative to the plane of polarization of the corresponding plane-polarized incident light beam. At least one such linear section lies substantially across the center of the transmitted excident light spot and extends substantially across the width of the transmitted excident light spot. The variation in the dispersion of the transmitted excident light spot for the at least four plane-polarized light beams is measured and a proxy variable for each reference material using the variation in measured dispersions at different planes of polarization for that reference material is evaluated. Finally, a correlation between the proxy variable and the known anisotropies of the reference materials and storing it as a known correlation is formed.

Figure 11:
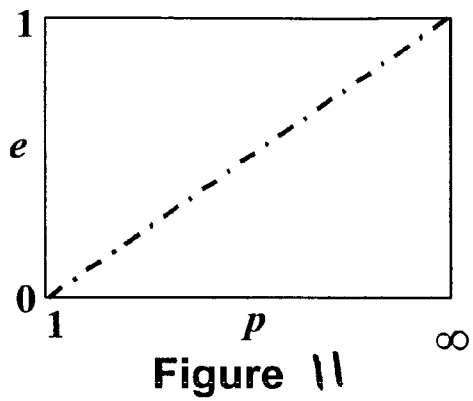
FIG. 11 is a correlation curve for anisotropy or fiber orientation index vs. a proxy variable.

FIG. 11 is a representative correlation curve for anisotropy (e) or fiber orientation index vs. a proxy variable (P). In this example, the curve shows that anisotropy increases monotonically with the value of the proxy variable.

By measuring the dispersions of polarized light at each of at least four planes of polarization, it is also possible to determine whether the fiber orientation distribution is symmetric and unimodal, or if it is asymmetric or multimodal. It is advantageous to employ more than four planes of polarization in the measurement if the distribution is expected to be significantly asymmetric or if it is expected to be multimodal.

Figure 23A:
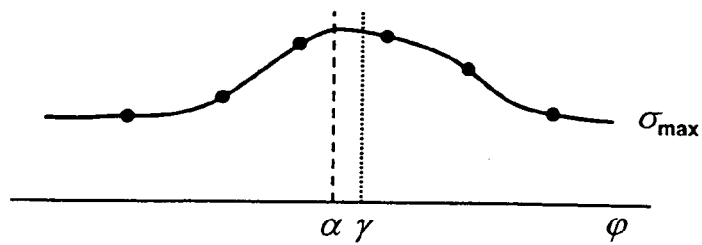
FIGS. 23A and 23B, respectively, are the Cartesian and polar plots of maximum dispersion vs. plane of polarization which depict an asymmetric fiber orientation distribution.
Figure 23B:
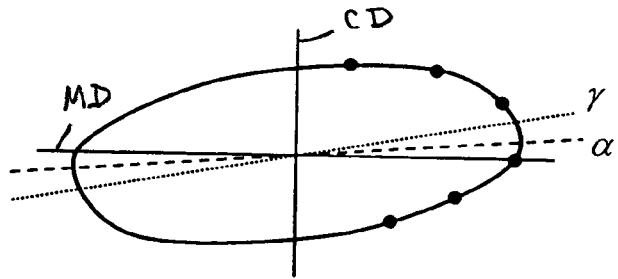

FIGS. 23A and 23B show the dispersion $\sigma_{max}$ measured in the plane of polarization at six planes of polarization $\phi$. The data are plotted both in Cartesian and polar forms, and a smooth curve has been drawn through the data points. The measured data lie in the right half plane of the polar plot, and the equivalence between a direction $\phi$ and its opposite $\phi+180°$ has been employed to complete the curve in the polar plot to the range 0° to 360°. The dispersion data and plotted curve are asymmetric, which means that the fiber orientation distribution is also asymmetric. The figures indicate two significant directions which can be estimated from the measurements, the direction of maximum fiber alignment $\alpha$, and the direction of average alignment $\gamma$. These directions coincide for symmetric distributions, and the difference between them is an indicator of the degree of asymmetry. Other indices can also be computed from the measurement, such as a skewness factor for the dispersion which represents the skewness of the fiber orientation distribution. The skewness factor complements the anisotropy factor for asymmetric distributions.

Figure 24A:
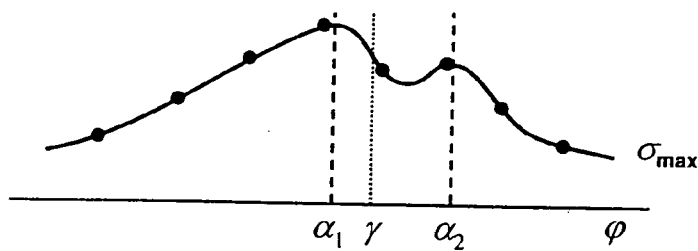
FIGS. 24A and 24B, respectively, are the Cartesian and polar plots of maximum dispersion vs. plane of polarization which depict a multimodal fiber orientation distribution.
Figure 24B:
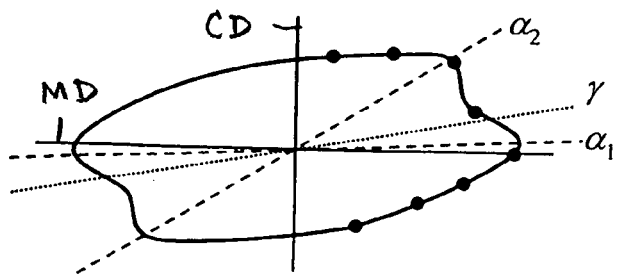

Similarly, FIGS. 24A and 24B show the dispersion $\sigma_{max}$ measured in the plane of polarization at eight planes of polarization $\phi$ in both Cartesian and polar forms, with a smooth curve drawn through the data points. In this case, the dispersion data and plotted curve are both asymmetric and multimodal, which means that the fiber orientation distribution is also asymmetric and multimodal. The figures indicate three significant directions which can be estimated from the measurements, the two directions at which the fiber alignment has local maxima $\alpha_1$, and $\alpha_2$, and the direction of average alignment $\gamma$. In the example shown, the multimodal distribution is bimodal, since it has two distinct maxima, but multimodal distributions can also have more than two distinct maxima. Indices of multimodality can be constructed for example from the angular and amplitude differences between their plural maxima.

While only the dispersion in the plane of polarization of each spot are measured in the examples of FIGS. 23A and 23B and FIGS. 24A and 24B it is possible to use additionally or alternatively measurements of dispersion perpendicular to or at other angles to the plane of polarization. The asymmetry and modes of the distribution can be quantified more accurately and more robustly using measurements of dispersion both in the plane of polarization and perpendicular to the plane of polarization for each spot.

FIGS. 6A to 6E, FIGS. 15 to 17, and FIGS. 23A, 23B, 24A and 23B depict apparatus and measurements in which the planes of polarization of the at least four spots span a wide range of polarization angles with substantially uniform angular spacing between the planes of polarization of the spots. In many cases, such an arrangement is preferred, so that the planes of polarization are substantially at uniform intervals spanning a broad range, such as from −75° to 75° with respect to the machine direction. However, the angular spacing between the planes of polarization need not be uniform, and the total angular span of the at least four polarization planes need not always be large. In particular, if it is expected that asymmetric or multimodal fiber orientation distributions will occur, then the planes of polarization can be advantageously at closer angular spacing in and near those ranges of angles which are expected to contain the maximum and average orientation angles.

Figure 12:
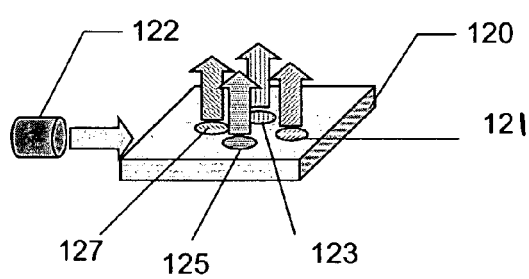
FIGS. 12, 13, and 14 depict various light source and polarizer arrangements.
Figure 13:
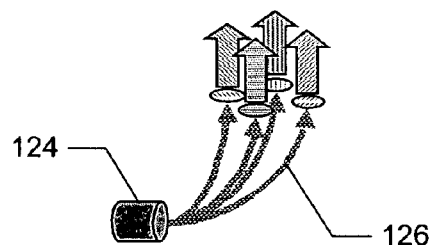
Figure 14:
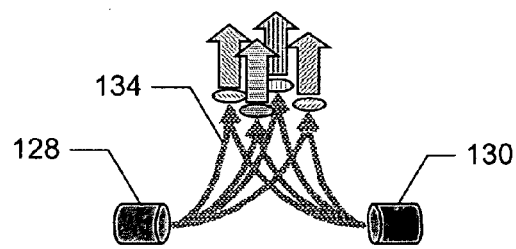
Figure 25:
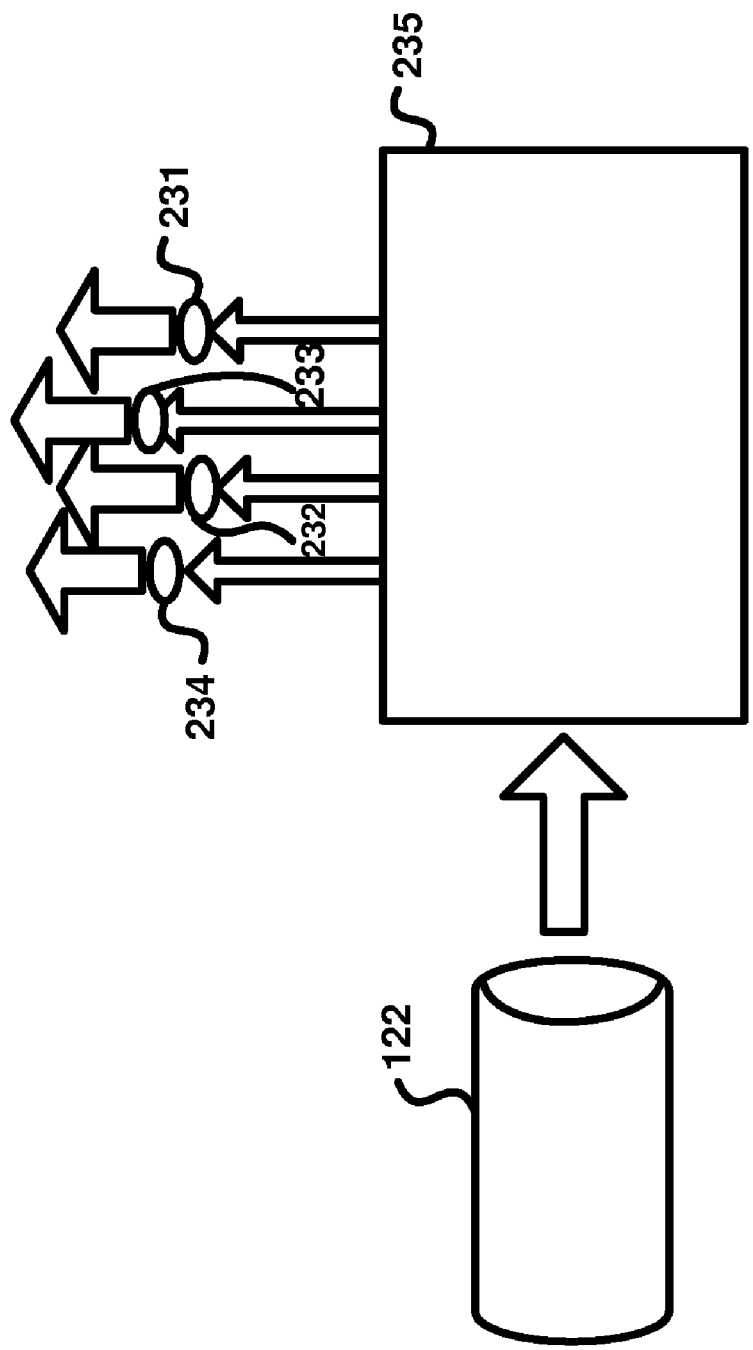
FIG. 25 depicts an arrangement containing a light source, a beam splitter and polarizers in one embodiment.
Figure 26:
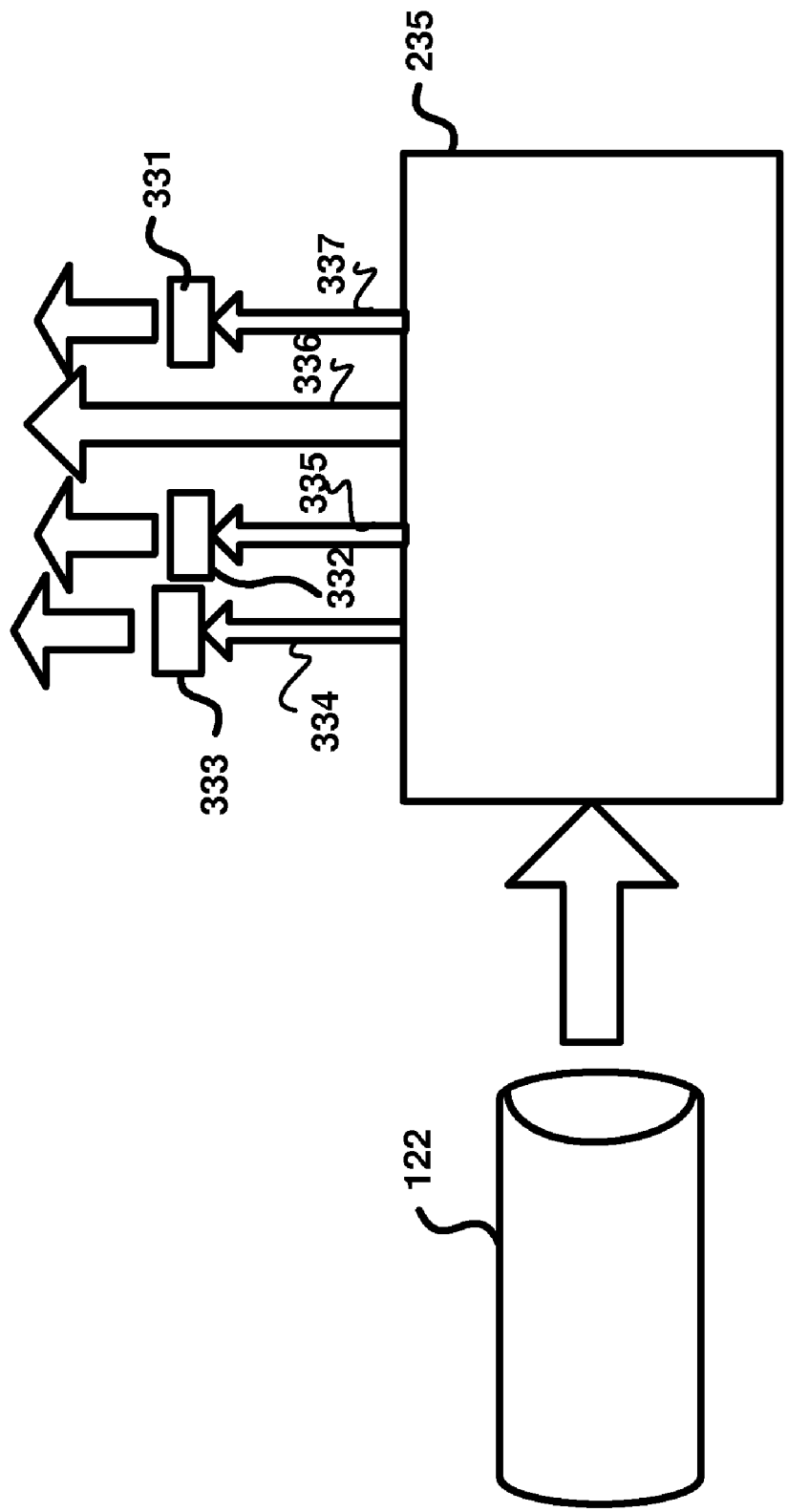
FIG. 26 depicts an arrangement containing a light source, a beam splitter and half-wave phase retarders/chiral material in one embodiment.

FIGS. 12, 13, and 14 illustrate alternative configurations for generating at least four linearly or plane-polarized light beam that can be directed onto a surface of a web being analyzed. FIG. 12 shows a compact array of polarized light sources that includes a light source 122 and a diffractive optic component 120 which has a plurality of polarizing elements 121, 123, 125, and 127. Light from the light source 122 is diffracted by a single diffractive optic component 120 which divides the input beam before each of the divided beams are polarized by the polarizing elements 121, 123, 125, and 127 to form four shaped excident beams in different polarization planes. Alternatively, instead of using a diffractive optic component, the single unpolarized collimated light beam can be divided by one or more beam splitters to form at least four light beams which are then each polarized by conventional means such as by different polarization filters. FIG. 25 depicts such an example configuration where light from light source 122 is divided by beam splitter 235 to form four light beams, which are then polarized by polarization filters 231–234. In another procedure, the polarization plane of only three of the four light beams from the beam splitter is altered, for example, by passing each of the three beams through at least one half-wave phase retarder or by passing each through a chiral material of known optical depth. FIG. 26 illustrates such a procedure, where the polarization plane of three (334, 335 and 337) of the four light beams (334 through 337) from beam splitter 235 is altered by passing each of the corresponding three beams through a corresponding half-wave phase retarder (333, 332 and 331 respectively). Alternatively, components 333, 332 and 331 may be constructed of a chiral material of known optical depth.

FIG. 13 shows a similar arrangement where light from source 124 is led through a set of light pipes 126, e.g., optical fibers, to an array of polarizing elements. FIG. 14 shows an arrangement that employs a pair of light sources 128, 130 and both contribute light through the plurality of light pipes 126 to the polarizing elements. With any of the arrangements, devices for collimating the light may also be provided. Also, devices for attenuating the light may be provided, so that the illumination intensity is essentially the same for each illuminated area, such as by using controllable liquid crystal arrays.

As is apparent, a plurality of light sources and polarizers can be employed, such that light from each light source passes through at least one polarizer and is used to illuminate at least one area of the web, and such that each area of the web is illuminated by polarized light from at least one light source. The intensity of illumination of each illuminated area can be controlled for example by regulating the power of the light sources.

Each of the light sources 122, 124, 128, and 130 preferably provides high intensity illumination that consists of a constant stream of energy within a wavelength required for measurement. The light source can be amplitude modulated by conventional mechanical devices such as choppers, shutters, tuning forks and the like to enhance the signal-to-noise ratio. Another exemplary modulating technique employs electro-optical shutters such as Kerr cells and Pockels cells that are positioned in the light beam path of the light source and acousto-optical devices such as acousto-optical tunable filters. Alternatively, direct modulation of a drive current that is coupled to the light source to generate pulsed illumination can be used.

Preferred light source devices include light-emitting diode (LED), laser diode, or an array of LEDs or laser diodes. When the light source is modulated to create a stroboscopic flash effect, for instance, a high modulation rate is preferred. The resulting short exposure times allow the imaging device, with correspondingly short integration times, to obtain better images of the image area by reducing or eliminating the adverse effects caused by motion-blurring in the direction of movement of the web. In the case of a charge-coupled device (CCD), a short integration time lets pixels collect less light and a longer integration time lets pixels collect more light. Alternatively, or in addition to modulating the light source, the imaging device, e.g., CCD camera, that operates at a high exposure rates, i.e., short integration times, can be selected. In this case, the illumination can be continuous which makes it is easier to maintain consistent illumination at different measurements.

Figure 15:
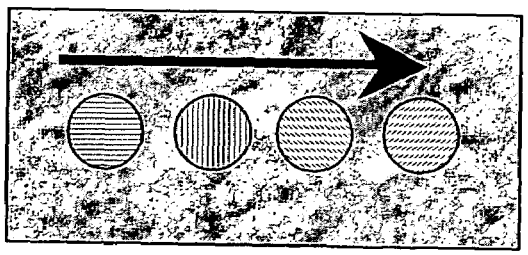
FIGS. 15, 16, and 17 depict various arrays of illumination spots on the web.

With the present invention at least four and preferably at least eight plane-polarized shaped beams of light, each with a different plane of polarization, are directed onto the web being analyzed. The illuminated spots can be arranged in different patterns in order to measure the fiber orientation at different positions of the web. For example, FIG. 15 illustrates four illuminated circular-shaped spots, each illuminated with a different plane of polarization, that are arranged as a linear array that is aligned in the direction of movement of the web. An image-based measurement device of the present invention employing this configuration of the illuminated spots, will measure essentially the same parts of the web, especially if the dispersions measured for each spot are filtered or averaged in time. This applies whether the device is stationary or is scanned across along the cross-direction web, since the speed of web movement is usually much faster than the traversing speed of the device.

Figure 16:
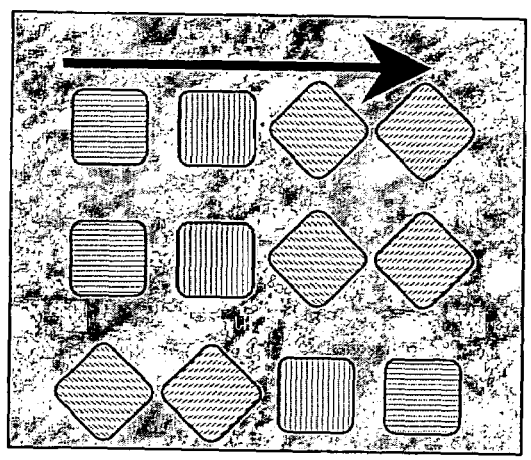

FIG. 16 illustrates a plurality of square-shaped spots that illuminate a surface of the web. The pattern includes three rows of spots with each row having spots that are each illuminated with a different plane of polarization. The spots in each row are arranged as a linear array that is aligned in the direction of movement of the web. The four spots of the top row have the shape arrangement and same plane of polarization as that of the four spots of the middle row. In this configuration, the three linear arrays of spots may be arranged within the imaged area on the web such that the fiber orientation is measured essentially simultaneously at several locations from a single image. This allows the fiber orientation to be measured over the whole web width using fewer cameras than measurement locations. It also allows the fiber orientation to be measured at higher spatial resolution with a scanning measurement device.

Figure 17:
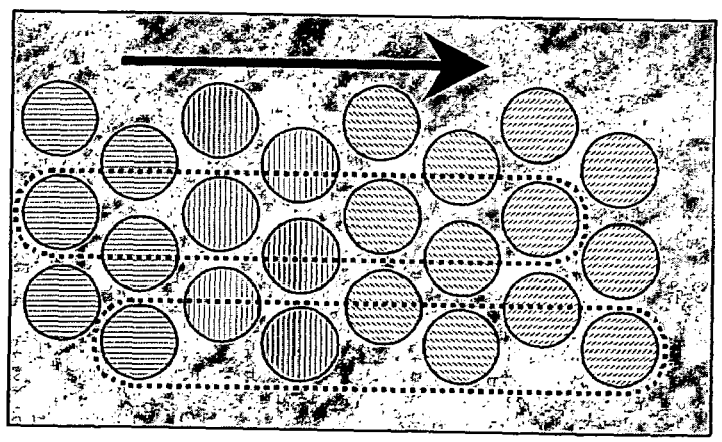

FIG. 17 illustrates a plurality of circular-shaped spots that are closely positioned together in the cross direction. In this case, six linear rows, each having four spots with each spot illuminated with a different plane of polarization, are arranged in a staggered pattern. The individual illuminated spots are closely spaced in the cross direction without interfering with each other. This arrangement allows a true average of fiber orientation to be evaluated over a part of the web, and the variation around that average to be conveniently expressed for subsets of a given width. For instance, from 50 arrays at 1 mm pitch, it is possible to evaluate the average over the 50 mm width and the standard deviation of 1 mm samples around that average.

The invention can be used to measure the fiber orientation at strategic locations throughout the papermaking process. A typical sheetmaking system for producing a continuous sheet of paper material has a plurality of actuators that are arranged to control discharge of wet stock from a headbox onto a supporting fourdrinier wire along the cross direction which is transverse to the machine direction of the moving paper material. The paper material which is a sheet of fibrous slurry that forms on top of the wire that is trained to travel in the MD between rollers located at front and back ends of fourdrinier wire and that passes through a calendaring stack.

Figure 18:
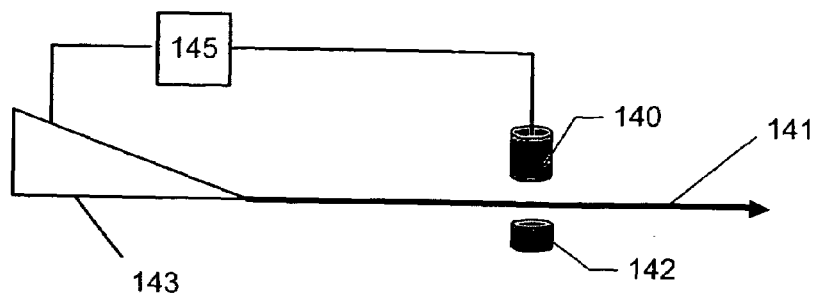
FIGS. 18, 19, 20, and 21 depict various light source and imaging device configurations.

FIG. 18 illustrates an embodiment of the apparatus for measuring the fiber orientation on a web 141 which is positionally constrained to travel in a relatively straight line without much fluttering, for instance, by tension or aerodynamics, as in the dry in of a papermaking machine. In this case, polarized light source array 142 illuminates the lower surface of the web 141 and imaging device, e.g., lens/camera, 140 detects images from the upper side of the web. The inventive fiber orientation measurement apparatus can further include a computer 145 that is connected to the imaging device 140 and actuators of the headbox 143. The computer 145 analyzes the digital images from the imaging device to estimate the fiber orientation of the paper 141. In addition, the computer 145 includes a profile analyzer which includes a control system that operates in response to the cross-directional measurements from the imaging device 140, as further described herein. In operation, imaging device 140 and polarized light source array 142 can be scanned in the cross direction to provide the computer 145 with digital images of the paper along the cross direction. From these images, signals that are indicative of the fiber orientation at various cross-directional measurement points are generated. The profile analyzer also includes software for controlling the operation of various components of the sheetmaking system, including, for example, the above described actuators of the headbox 143. Depending on the degree of deviation of the fiber orientation from a desired set point, wet end and/or dry end parameters can be adjusted accordingly to change the fiber orientation.

For example, the fiber orientation profile in paper can be altered by distorting the shape of the headbox slice lip or by changing the inlet flow profile from a manifold to the headbox. In both cases, the velocity field of the jet of slurry to the wire is altered, such that the fiber orientation profile and other properties of the paper are changed. Thus, multiple parameters, e.g., slice lip configuration and manifold inlet flow profile, can be manipulated in order to control the fiber orientation of a web.

As is apparent, the present invention provides a method of on-line measuring the fiber orientation of a moving web by analyzing digital images thereof. Empirical data derived from this technique can be employed for process modeling, simulation and control of a sheetmaking system for making products comprising nonwoven materials. A method of developing a mathematical model is to stimulate or perturb the sheetmaking process and measuring the responses, i.e., changes in the fiber orientation, if any, that result. For example, the slice lip and/or manifold can be manipulated at different levels and the responses measured. The mathematical models can be used to regulate the system in order to control the fiber orientation of the sheet. Process control techniques for papermaking machines are further described, for instance, in U.S. Pat. No. 6,805,899 to MacHattie et al., U.S. Pat. No. 6,466,839 to Heaven et al., U.S. Pat. No. 6,149,770, to Hu et al., U.S. Pat. No. 6,092,003 to Hagart-Alexander et. al., U.S. Pat. No. 6,080,278 to Heaven et al., U.S. Pat. No. 6,059,931 to Hu et al., U.S. Pat. No. 6,853,543 to Hu et al., and U.S. Pat. No. 5,892,679 to He, which are all incorporated herein by reference.

The fiber orientation of a moving web can be monitored both in the cross direction and the machine direction. In the latter scenario, multiple apparatus can be positioned in tandem in the MD along suitable positions of a papermaking machine to optimize papermaking machines. A continuous fiber orientation profile of the paper stock on the web can be generated compared to an "ideal" profile for making a particular grade of paper. Although the fiber orientation of the web is largely determined in the forming process on the wire, it is modified during the drying process. In particular, when the sheet moisture content falls below 40%, the sheet begins to shrink on further drying. This shrinkage is non-uniform in the CD axis and is most pronounced near the free edges of the sheet, which are not positionally restrained. However, the shrinkage is countered by plastic and elastic extension in the MD axis due to the tension which transports the sheet. Thus, the orientation angle distribution is changed by geometric distortion of the web, and this distortion is not uniform across the sheet. The shrinkage, orientation, tension, and elongation are all coupled to the evolution of the moisture profile. Depending on the degree of deviation from ideal, wet end and/or dry end parameters can be adjusted accordingly. See, for example, U.S. Pat. No. 6,092,003 to Hagart-Alexander which is incorporated herein.

Similarly, for CD measurements, an array of apparatuses can be positioned along the CD at any suitable position of the papermaking machine. Alternatively, a scanning system that includes single apparatus that is scanned across the width of a web can be employed. Scanner systems generally includes pairs of horizontally extending guide tracks that span the width of the paper product to be monitored. The sensor is secured to a carriage that moves back-and-forth over the paper product as measurements are made. On-line scanning sensor systems for papermaking manufacture are disclosed in U.S. Pat. No. 4,879,471 to Dahlquist, U.S. Pat. No. 5,094,535 to Dahlquist et al., and U.S. Pat. No. 5,166,748 to Dahlquist, all of which are incorporated herein by reference.

A light source array and camera may traverse the sheet together in coordination, such that substantially the whole width of the sheet is measured sequentially. Alternatively, a plurality of stationary light source arrays and cameras may be deployed across the sheet, such that each such arrangement measures a particular location. Alternatively, a plurality of mobile light source arrays and cameras may each traverse a part of the sheet, such that essentially the whole sheet is measured.

Figure 19:
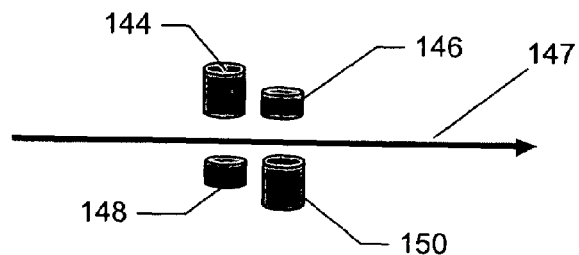

FIG. 19 illustrates an embodiment of the apparatus for measuring the fiber orientation on a web 147 which is particularly suited for measuring the fiber orientations from both the top side and bottom side of the web. In this case, polarized light source arrays 146 and 148 illuminates the upper and lower surfaces, respectively, of the web 147 and imaging devices 150 and 144 detect images from the lower and upper sides, respectively, of the web. Fiber orientation profiles can be produced simultaneously. These measurements are directly or indirectly linked to other sheet properties like strength and/or web tension and/or shrinkage and elongation and/or sheet curl and twist. By making calibration fiber orientation measurements using paper having known sheet properties, a library can be established to correlate fiber orientation measurements to actual strength, web tension, shrinkage, twist or curl, and other characteristics.

Figure 20:
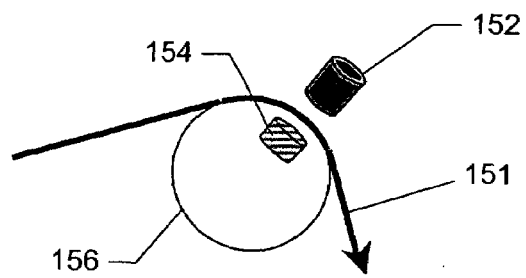

FIG. 20 illustrates the inventive apparatus being deployed to measure the fiber orientation of paper 151 as it moves over a rotation support 156 which can be a roller, dryer cylinder, and the like and which is made of at least partially transparent material. In this embodiment, the apparatus includes (i) a stationary polarized light source 154 that directs polarized radiation through the rotation support 156 and onto the web 151 and (ii) imaging device 152, e.g., lens/camera.

Figure 21:
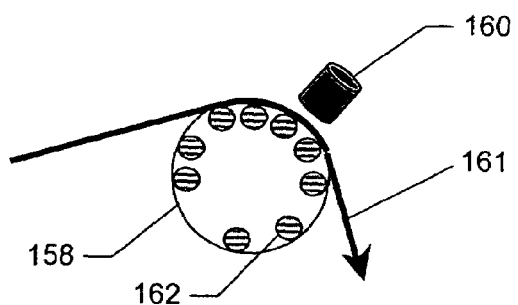
Figure 22:
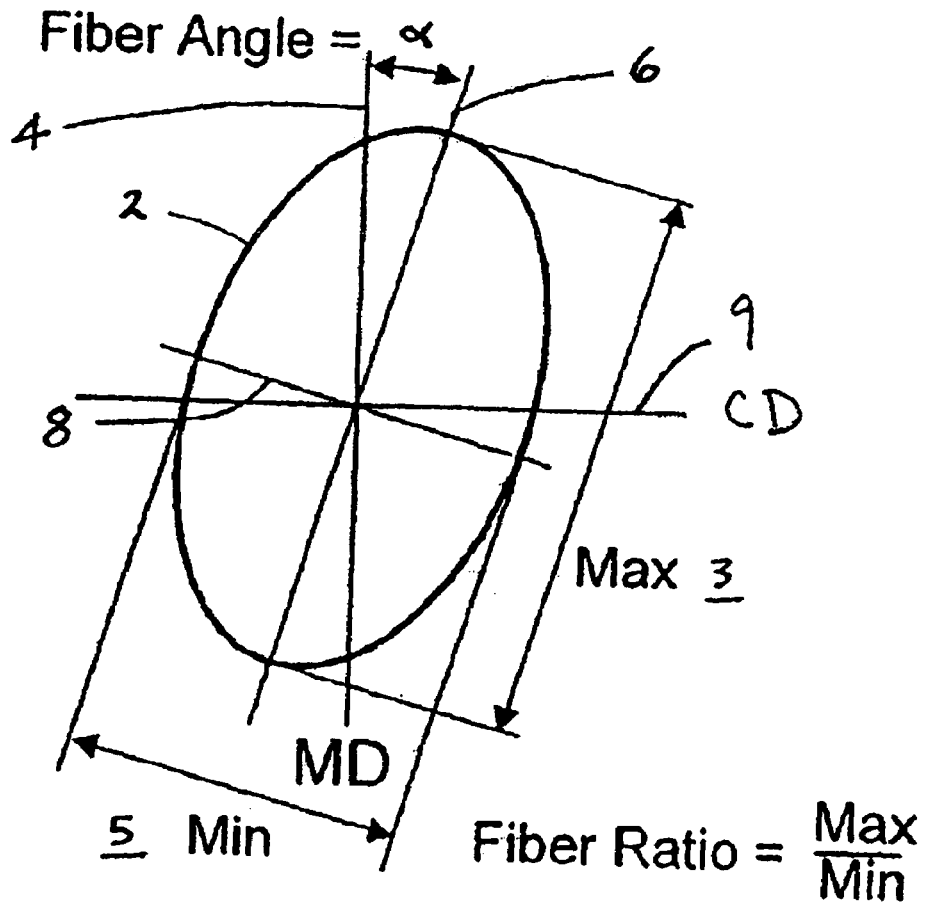
FIG. 22 depicts the definition of fiber orientation measurement.

FIG. 21 illustrates a similar apparatus being deployed to measure the fiber orientation of paper 161 as it moves over a rotation support 158 wherein a plurality of polarized light sources 162 are arranged in a defined pattern or array on the inner surface of the rotation support 158. Operation of the imaging device 160, that is positioned on the other side of the web 161, is synchronized with the rotation of plurality of polarized light sources 162.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A method for measuring the fiber orientation of a moving web that comprises the steps of:
(a) illuminating essentially simultaneously at least four light spots on a first side of the web with at least four plane-polarized incident light beams having different polarization characteristics, wherein each of the at least four plane-polarized light beams is incident substantially perpendicular to the web surface and is transmitted through the web to produce at least four corresponding transmitted excident light spots on a second side of the web that is opposite to the first side;
(b) for each of the at least four plane-polarized light beams, measuring the dispersion of the excident light spot along at least one linear section which is at a known angle relative to the plane of polarization of the corresponding plane-polarized incident light beam, wherein at least one such linear section lies substantially across the center of the transmitted excident light spot and extends substantially across the width of the transmitted excident light spot;
(c) calculating variations, if any, in the dispersion of the transmitted excident light spot for the at least four plane-polarized light beams; and
(d) estimating the fiber orientation of the web from the variations.

2. The method of claim 1 wherein step (b) comprises obtaining an image of an illuminated area on the second side of the web wherein the illuminated area contains the transmitted excident light spots from the at least four incident light beams.

3. The method of claim 1 wherein the fiber orientation is characterized as an average fiber orientation angle or an index of fiber orientation anisotropy.

4. The method of claim 1 wherein the fiber orientation is characterized as a statistical distribution of orientation angles.

5. The method of claim 4 wherein the fiber orientation is further characterized as a skewness index or asymmetry index of the statistical distribution of orientation angles.

6. The method of claim 4 wherein the fiber orientation is further characterized as at least one angle for which there is a local maximum in the statistical distribution of orientation angles.

7. The method of claim 1 wherein in step (b) for each of the at least four plane-polarized light beams, the dispersion of the excident light spot is measured (i) along a linear section that is at an angle which substantially coincides with the plane of polarization of the incident light beam, or (ii) along a linear section that is at an angle which is substantially perpendicular with the plane of polarization of the incident light beam, or (iii) along a first linear section that is at an angle which substantially coincides with the plane of polarization of the incident light beam and along a second linear section that is at an angle which is substantially perpendicular with the plane of polarization of the incident light beam.

8. The method of claim 1 wherein for step (d) the fiber orientation is estimated from the variation in the dispersions of transmitted excident light spots, the dispersions measured for each spot along a first linear section which substantially coincides with the plane of polarization of the incident light beam and along a second linear section which is substantially perpendicular to the plane of polarization of the incident light beam.

9. The method of claim 1 wherein each of the at least four plane-polarized incident light beams has a substantially rectangular or piecewise rectangular cross-section, such that opposite sides of each plane-polarized incident light beam are substantially parallel.

10. The method of claim 9 wherein the plane of polarization of each rectangular spot of incident light is substantially parallel to one of the sides of the spot.

11. The method of claim 9 wherein the dispersion of the excident light spot is measured along a plurality of parallel linear sections that are at a known angle relative to the plane of polarization of the corresponding plane-polarized incident light beam such that the plurality of parallel linear sections all intersect each transmitted excident light spot.

12. The method of claim 1 wherein the moving web has at least two layers and the method further comprises employing at least two different wavelengths of plane-polarized light and the fiber orientations for at least two layers of the web are estimated from measurements of the variations in dispersion of the excident light spots at the at least two different wavelengths.

13. The method of claim 1 wherein steps (a) through (c) forms a first set of measurements of dispersion of polarized light that are made for transmission of light spots from a first side of the web to a second side opposite the first side, and the method further comprises establishing a second set of measurements by the following steps (e) through (g) which comprises:

(e) illuminating essentially simultaneously at least four second light spots on the second side of the web with at least four second plane-polarized incident light beams having different polarization characteristics, wherein each of the at least second four plane-polarized light beams is incident substantially perpendicular to the web surface and is transmitted through the web to produce at least four corresponding transmitted second excident light spots on the first side of the web;

(f) for each of the at least four second plane-polarized light beams, measuring the dispersion of the second excident light spot along at least one linear section which is at a known angle relative to the plane of polarization of the corresponding second plane-polarized incident light beam, wherein at least one such linear section lies substantially across the center of the transmitted second excident light spot and extends substantially across the width of the transmitted second excident light spot;

(g) calculating variations, if any, in the dispersion of the transmitted excident light spot for the at least four second plane-polarized light beams; and wherein step (d) comprises estimating the fiber orientation for at least one surface layer of the web from the variations in dispersion in the first and second sets of measurements.

14. The method of claim 1 further comprising normalized dispersions by normalizing each measured dispersion value with a known reference dispersion value that is measured along a corresponding linear section that lies substantially across the center of a corresponding transmitted excident light spot and extends substantially across the width of the transmitted excident light spot and estimating the fiber orientation of the web from the variations, if any, in the normalized dispersions.

15. The method of claim 14 further comprising calibration steps of:

(i) providing a substantially planar isotropic translucent reference material;

(ii) illuminating essentially simultaneously at least four light spots on a first side of the reference material with at least four plane-polarized incident light beams having different polarization characteristics, wherein each of the at least four plane-polarized light beams is incident substantially perpendicular to the reference material surface and is transmitted through the reference material to produce at least four corresponding transmitted excident light spots on a second side of the reference material that is opposite to the first side;

(iii) for each of the at least four plane-polarized light beams, measuring the dispersion of the excident light spot along at least one linear section which is at a known angle relative to the plane of polarization of the corresponding plane-polarized incident light beam, wherein at least one such linear section lies substantially across the center of the transmitted excident light spot and extends substantially across the width of the transmitted excident light spot, with the proviso that for each of the at least four plane-polarized light beams in this step (iii) the dispersion of the transmitted excident light spot along at least all of the at least one linear sections used in measuring the fiber orientation of the web in steps (a) and (b) of claim 1 are measured;

(iv) calculating variations, if any, in the dispersion of the transmitted excident light spot for the at least four plane-polarized light beams; and (v) storing the measured dispersions as known reference dispersions for each section through each of the at least four plane-polarized light beams.

16. The method of claim 1 comprising evaluating a proxy variable from measured dispersions of the transmitted excident light spots in step (b) and estimating the fiber orientation of the web from the proxy variable with a known correlation.

17. The method of claim 16 further comprising calibration steps of:

(i) providing at least two substantially planar anisotropic translucent reference materials with known anisotropies;

(ii) for each reference material:

(1) illuminating essentially simultaneously at least four light spots on a first side of the reference material with at least four plane-polarized incident light beams having different polarization characteristics, wherein each of the at least four plane-polarized light beams is incident substantially perpendicular to the reference material surface and is transmitted through the reference material to produce at least four corresponding transmitted excident light spots on a second side of the reference material that is opposite to the first side;

(2) for each of the at least four plane-polarized light beams, measuring the dispersion of the excident light spot along at least one linear section which is at a known angle relative to the plane of polarization of the corresponding plane-polarized incident light beam, wherein at least one such linear section lies substantially across the center of the transmitted excident light spot and extends substantially across the width of the transmitted excident light spot, with the proviso that for each of the at least four plane-polarized light beams in this substep (2) of step (ii) the dispersion of the transmitted excident light spot along at least all of the at least one linear sections used in measuring the fiber orientation of the web in steps (a) and (b) of claim 1 are measured;

(3) calculating variations, if any, in the dispersion of the transmitted excident light spot for the at least four plane-polarized light beams; and (iii) evaluating a proxy variable for each reference material using the variation in measured dispersions at different planes of polarization for that reference material; and (iv) forming a correlation between the proxy variable and the known anisotropies of the reference materials and storing it as a known correlation.

18. The method of claim 17 wherein the proxy variable is one of (i) the ratio of the largest dispersion in the plane of polarization to the smallest dispersion in the plane of polarization, (ii) the ratio of the largest dispersion perpendicular to the plane of polarization to the smallest dispersion perpendicular to the plane of polarization, (iii) the ratio of the largest dispersion in the plane of polarization for any spot to the smallest dispersion perpendicular to the plane of polarization for any spot, (iv) the largest ratio of the dispersion in the plane of polarization to the dispersion perpendicular to the plane of polarization for the same spot, (v) the smallest ratio of the dispersion in the plane of polarization to the dispersion perpendicular to the plane of polarization for the same spot.

19. The method of claim 1 wherein in step (b) measuring the dispersion of the excident light spot along at least one linear section comprises estimating the dispersion from parts of a linear section where illumination intensity is not uniform.

20. The method of claim 1 wherein the at least four plane-polarized incident light beams are formed by:
  (i) dividing a single unpolarized collimated light beam with at least one beam splitter; and
  (ii) polarizing each of the divided light beams, such that at least four of the resulting beams have different planes of polarization.

21. The method of claim 1 wherein the at least four plane-polarized incident light beams are formed by:
  (i) dividing a single unpolarized collimated light beam with a beam splitter; and
  (ii) altering the polarization plane of at least three of the resulting light beams by (a) passing each of at least three beams through at least one half-wave phase retarder or (b) passing each of at least three beams through a chiral material of known optical depth.

22. The method of claim 1 wherein the characteristics of the incident light beams are adjusted by altering at least one of (i) the cross-sectional width of the at least four plane-polarized light beams, (ii) the cross-sectional shape of the at least four plane-polarized light beams, or (iii) the intensities of the at least four plane-polarized light beams.

23. The method of claim 1 wherein the at least four illuminated spots are arranged substantially in the direction of movement of the web.

24. The method of claim 2 wherein the image is an average of a plurality of sequential images that are created at separate measuring instants.

25. A system for measuring the fiber orientation of a web that comprises:
  means for illuminating at least four light spots essentially simultaneously on a first side of the web with at least four plane-polarized incident light beams having different polarization characteristics, wherein each of the at least four plane-polarized light beams is incident substantially perpendicular to the web surface and is transmitted through the web to produce at least four corresponding transmitted excident light spots on a second side of the web that is opposite to the first side;
  image obtaining means for obtaining at least one image of an illuminated area on the second side of the web wherein the illuminated area contains the transmitted excident light spots from the at least four incident light beams;
  control means associated with each of the at least four plane-polarized light beams for measuring the dispersion of the excident light spot along at least one linear section which is at a known angle relative to the plane of polarization of the corresponding plane-polarized incident light beam, wherein at least one such linear section lies substantially across the center of the transmitted excident light spot and extends substantially across the width of the transmitted excident light spot;
  means for calculating variations, if any, in the dispersion of the transmitted excident light spot for the at least four plane-polarized light beams; and
  means for estimating the fiber orientation of the web from the variations.

26. The system of claim 25 wherein the fiber orientation is characterized as an average fiber orientation angle or an index of fiber orientation anisotropy.

27. The system of claim 25 wherein the fiber orientation is characterized as a statistical distribution of orientation angles.

28. The system of claim 27 wherein the fiber orientation is further characterized as a skewness index or asymmetry index of the statistical distribution of orientation angles.

29. The system of claim 27 wherein the fiber orientation is further characterized as at least one angle for which there is a local maximum in the statistical distribution of orientation angles.

30. The system of claim 25 wherein for each of the at least four plane-polarized light beams, the dispersion of the excident light spot is measured (i) along a linear section that is at an angle which substantially coincides with the plane of polarization of the incident light beam, or (ii) along a linear section that is at an angle which is substantially perpendicular with the plane of polarization of the incident light beam, or (iii) along a first linear section that is at an angle which substantially coincides with the plane of polarization of the incident light beam and along a second linear section that is at an angle which is substantially perpendicular with the plane of polarization of the incident light beam.

31. The system of claim 25 wherein the fiber orientation is estimated from the variation in the dispersions of transmitted excident light spots, the dispersions measured for each spot along a first linear section which substantially coincides with the plane of polarization of the incident light beam and along a second linear section which is substantially perpendicular to the plane of polarization of the incident light beam.

32. The system of claim 25 wherein each of the at least four plane-polarized incident light beams has a substantially rectangular or piecewise rectangular cross-section, such that opposite sides of each plane-polarized incident light beam are substantially parallel.

33. The system of claim 32 wherein the plane of polarization of each rectangular spot of incident light is substantially parallel to one of the sides of the spot.

34. The system of claim 32 wherein the dispersion of the excident light spot is measured along a plurality of parallel linear sections that are at a known angle relative to the plane of polarization of the corresponding plane-polarized incident light beam such that the plurality of parallel linear sections all intersect each transmitted excident light.

35. The system of claim 25 wherein the moving web has at least two layers and the system employs at least two different wavelengths of plane-polarized light and the means for estimating the fiber orientation estimates the fiber orientations for at least two layers of the web from measurements of the variations in dispersion of the excident light spots at the at least two different wavelengths.

36. The system of claim 25 further comprising:
means for illuminating at least four second light spots essentially simultaneously on the second side of the web with at least four second plane-polarized incident light beams having different polarization characteristics, wherein each of the at least four second plane-polarized light beams is incident substantially perpendicular to the web surface and is transmitted through the web to produce at least four corresponding transmitted second excident light spots on the first side of the web;
image obtaining means for obtaining at least one image of a second illuminated area on the first side of the web wherein the second illuminated area contains the transmitted second excident light spots from the at least four second incident light beams;
control means associated with each of the at least four second plane-polarized light beams for measuring the dispersion of the second excident light spot along at least one linear section which is at a known angle relative to the plane of polarization of the corresponding second plane-polarized incident light beam, wherein at least one such linear section lies substantially across the center of the transmitted second excident light spot and extends substantially across the width of the transmitted second excident light spot; and
means for calculating variations, if any, in the dispersion of the transmitted second excident light spot for the at least four second plane-polarized light beams; and
wherein the means for estimating the fiber orientation of the web estimates the fiber orientation for at least one surface layer of the web from variations in the dispersions in the transmitted excident light spots and from variations in the dispersions in the transmitted second excident light spots.

37. The system of claim 25 wherein the means for illuminating at least four light spots comprises:
(i) a source of single unpolarized collimated light beam;
(ii) a beam splitter that divides the single unpolarized collimated light beam into a plurality of light beams; and
(iii) means for polarizing the plurality of light beams to generate at least four beams that have different planes of polarization.

38. The system of claim 25 wherein the means for illuminating at least four light spots comprises:
(i) a source of single unpolarized collimated light beam;
(ii) a beam splitter that divides the single unpolarized collimated light beam into a plurality of light beams; and
(iii) at least one half-wave phase retarder through which at least three of the light beams are passed to alter the polarization plane of the at least three light beams.

39. The system of claim 25 wherein the means for illuminating at least four light spots comprises:
(i) a source of single unpolarized collimated light beam;
(ii) a beam splitter that divides the single unpolarized collimated light beam into a plurality of light beams; and
(iii) a chiral material of known optical depth through which at least three of the light beams are passed to alter the polarization plane of the at least three light beams.

40. The system of claim 25 wherein the at least four illuminated spots are arranged substantially in the direction of movement of the web.

41. The system of claim 26 wherein the image obtaining means generates an image of the illuminated area that is an average of a plurality of sequential images that are created at separate measuring instants.

* * * * *